US012590136B2

(12) United States Patent
Mann et al.

(10) Patent No.: US 12,590,136 B2
(45) Date of Patent: Mar. 31, 2026

(54) ENGINEERED T CELLS

(71) Applicants: Regeneron Pharmaceuticals, Inc., Tarrytown, NY (US); MEDIGENE IMMUNOTHERAPIES GMBH, Planegg-Martinsried (DE)

(72) Inventors: Jasdeep Mann, Lake Forest Park, WA (US); Christian Ellinger, Munich (DE); Daniel Sommermeyer, Munich (DE); Benjamin Boyerinas, Brookline, MA (US)

(73) Assignees: Regeneron Pharmaceuticals, Inc., Tarrytown, NY (US); MEDIGENE IMMUNOTHERAPIES GMBH, Planegg-Martinsried (DE)

( * ) Notice: Subject to any disclaimer, the term of this patent is extended or adjusted under 35 U.S.C. 154(b) by 1045 days.

(21) Appl. No.: 17/608,860

(22) PCT Filed: May 7, 2020

(86) PCT No.: PCT/US2020/031796
§ 371 (c)(1),
(2) Date: Nov. 4, 2021

(87) PCT Pub. No.: WO2020/227483
PCT Pub. Date: Nov. 12, 2020

(65) Prior Publication Data
US 2023/0044580 A1 Feb. 9, 2023

Related U.S. Application Data

(60) Provisional application No. 62/845,311, filed on May 8, 2019.

(51) Int. Cl.
*A61K 35/17* (2025.01)
*A61K 39/00* (2006.01)
(Continued)

(52) U.S. Cl.
CPC .......... *C07K 14/7051* (2013.01); *A61K 35/17* (2013.01); *A61K 39/001134* (2018.08);
(Continued)

(58) Field of Classification Search
None
See application file for complete search history.

(56) References Cited

U.S. PATENT DOCUMENTS

| | | | |
|---|---|---|---|
| 4,751,180 | A | 6/1988 | Cousens et al. |
| 4,935,233 | A | 6/1990 | Bell et al. |

(Continued)

FOREIGN PATENT DOCUMENTS

| | | |
|---|---|---|
| JP | 2009-514541 | 4/2009 |
| JP | 2016-520302 | 7/2016 |

(Continued)

OTHER PUBLICATIONS

Benjamin Boyerinas, et al; Abstract 602: A novel TGF-β/IL-12R signal conversion platform that protects CAR T cells from TGF-β-mediated immune suppression and concurrently amplifies effector function. Cancer Res Jul. 1, 2017; 77 (13_Supplement): 602. (Year: 2017).*

(Continued)

*Primary Examiner* — Evelyn Y Pyla
*Assistant Examiner* — Jagamya Vijayaraghavan
(74) *Attorney, Agent, or Firm* — Foley Hoag LLP; Amy E. Mandragouras; Ariana D. Harris

(57) ABSTRACT

The present disclosure provides improved compositions for adoptive T cell therapies for treating, preventing, or ameliorating at least one symptom of a cancer, infectious disease, autoimmune disease, inflammatory disease, and immunodeficiency, or condition associated therewith.

48 Claims, 5 Drawing Sheets

Specification includes a Sequence Listing.

(51) Int. Cl.

| | | |
|---|---|---|
| A61K 40/11 | (2025.01) | |
| A61K 40/32 | (2025.01) | |
| A61K 40/42 | (2025.01) | |
| A61P 35/00 | (2006.01) | |
| C07K 14/005 | (2006.01) | |
| C07K 14/705 | (2006.01) | |
| C07K 14/71 | (2006.01) | |
| C07K 14/715 | (2006.01) | |
| C07K 14/725 | (2006.01) | |
| C12N 5/0783 | (2010.01) | |
| A61K 38/00 | (2006.01) | |

(52) U.S. Cl.

CPC ................. *A61K 39/001136* (2018.08); *A61K 39/001186* (2018.08); *A61K 40/11* (2025.01); *A61K 40/32* (2025.01); *A61K 40/4229* (2025.01); *A61K 40/4234* (2025.01); *A61K 40/4268* (2025.01); *A61P 35/00* (2018.01); *C07K 14/005* (2013.01); *C07K 14/70596* (2013.01); *C07K 14/71* (2013.01); *C07K 14/7155* (2013.01); *C07K 14/7156* (2013.01); *C12N 5/0636* (2013.01); *A61K 38/00* (2013.01); *A61K 2239/31* (2023.05); *A61K 2239/38* (2023.05); *C07K 2319/02* (2013.01); *C07K 2319/03* (2013.01); *C07K 2319/33* (2013.01)

(56) References Cited

U.S. PATENT DOCUMENTS

| | | | |
|---|---|---|---|
| 5,994,136 | A | 11/1999 | Naldini et al. |
| 6,013,516 | A | 1/2000 | Verma et al. |
| 6,682,907 | B1 | 1/2004 | Charneau et al. |
| 6,692,736 | B2 | 2/2004 | Yu et al. |
| 7,157,091 | B1 | 1/2007 | Van Snick et al. |
| 7,311,914 | B2 | 12/2007 | Zhang et al. |
| 11,654,158 | B2 | 5/2023 | Boyerinas |
| 12,344,654 | B2 | 7/2025 | Ellinger et al. |
| 12,365,711 | B2 | 7/2025 | Boyerinas |
| 2009/0222936 | A1 | 9/2009 | Richmond et al. |
| 2015/0246959 | A1 | 9/2015 | Robbins et al. |
| 2015/0266973 | A1 | 9/2015 | Jarjour et al. |
| 2015/0307585 | A1 | 10/2015 | Blankenstein et al. |
| 2016/0075755 | A1 | 3/2016 | Valdes et al. |
| 2017/0036091 | A1 | 2/2017 | Hooper et al. |
| 2017/0267737 | A1 | 9/2017 | Protzer et al. |
| 2017/0360913 | A1 | 12/2017 | Zhao et al. |
| 2018/0024479 | A1 | 1/2018 | Yamada et al. |
| 2018/0244797 | A1 | 8/2018 | Pule et al. |
| 2019/0350974 | A1 | 11/2019 | Boyerinas |
| 2023/0159612 | A1 | 5/2023 | Ellinger et al. |
| 2023/0364141 | A1 | 11/2023 | Boyerinas |

FOREIGN PATENT DOCUMENTS

| | | | | |
|---|---|---|---|---|
| WO | WO 03/020763 | | 3/2003 | |
| WO | WO 2007/054250 | | 5/2007 | |
| WO | WO-2008/053573 | A1 | 5/2008 | |
| WO | WO-2011/024791 | A1 | 3/2011 | |
| WO | WO 2012/006635 | | 1/2012 | |
| WO | WO 2012/138858 | | 10/2012 | |
| WO | WO-2013/112942 | A1 | 8/2013 | |
| WO | WO 2014/172584 | | 10/2014 | |
| WO | WO 2015/017214 | | 2/2015 | |
| WO | WO-2016/120789 | A1 | 8/2016 | |
| WO | WO 2016/122738 | | 8/2016 | |
| WO | WO-2016/156202 | A1 | 10/2016 | |
| WO | WO 2016/164089 | | 10/2016 | |
| WO | WO-2016/199141 | A2 | 12/2016 | |
| WO | WO 2017/029512 | | 2/2017 | |
| WO | WO 2017/158103 | | 9/2017 | |
| WO | WO 2017/174824 | | 10/2017 | |
| WO | WO 2017/175006 | | 10/2017 | |
| WO | WO-2017174824 | A1 * | 10/2017 | ............ A61K 35/17 |
| WO | WO-2018/006005 | A1 | 1/2018 | |
| WO | WO 2018/067618 | | 4/2018 | |
| WO | WO 2018/094244 | | 5/2018 | |
| WO | WO 2019/036688 | | 2/2019 | |
| WO | WO-2019/070755 | A1 | 4/2019 | |
| WO | WO-2019/238023 | A1 | 12/2019 | |
| WO | WO-2020/193767 | A1 | 10/2020 | |
| WO | WO-2020/227483 | A1 | 11/2020 | |

OTHER PUBLICATIONS

Yang et al., Gene Ther. Nov. 2008;15(21):1411-23. doi: 10.1038/gt.2008.90. Epub May 22, 2008. PMID: 18496571; PMCID: PMC2684456. (Year: 2008).*

Yang Q, Jeremiah Bell J, Bhandoola A. T-cell lineage determination. Immunol Rev. Nov. 2010;238(1):12-22. doi: 10.1111/j.1600-065X.2010.00956.x. PMID: 20969581; PMCID: PMC2972740. (Year: 2010).*

Presky et al., Proc Natl Acad Sci U S A. Nov. 26, 1996;93(24):14002-7. doi: 10.1073/pnas.93.24.14002. PMID: 8943050; PMCID: PMC19484. (Year: 1996).*

Dotto GP, Rustgi AK. Squamous Cell Cancers: A Unified Perspective on Biology and Genetics. Cancer Cell. May 9, 2016;29(5):622-637. doi: 10.1016/j.ccell.2016.04.004. PMID: 27165741; PMCID: PMC4870309. (Year: 2016).*

Asao et al., "Cutting Edge: The Common γ-Chain Is an Indispensable Subunit of the IL-21 Receptor Complex," The Journal of Immunology, 2001, 167, 1-5.

Bhan et al., "MAGEA4 induces growth in normal oral keratinocytes by inhibiting growth arrest and apoptosis," Oncol Rep. Oct. 2012;28(4):1498-502.

Bird, Robert E., et al. "Single-chain antigen-binding proteins." Science (1988); 242.4877: 423-427.

Brichard et al., "Cancer regression and neurological toxicity cases after anti-MAGE-A3 TCR gene therapy," J Immunother. Feb. 2013;36(2):79-81.

Cameron et al., "Identification of a Titin-derived HLA-A1-presented peptide as a cross-reactive target for engineered MAGE A3-directed T cells," Sci Transl Med. Aug. 7, 2013;5(197):197ra103.

Challita, P. et al., "Multiple modifications in cis elements of the long terminal repeat of retroviral vectors lead to increased expression and decreased DNA methylation in embryonic carcinoma cells." J Virol. (1995); 69(2): 748-755.

Chaudhary, Vijay K., et al. "A rapid method of cloning functional variable-region antibody genes in *Escherichia coli* as single-chain immunotoxins." Proceedings of the National Academy of Sciences (1990); 87.3: 1066-1070 (and correction).

Cheung et al., "Accessory Protein-Like Is Essential for IL-18-Mediated Signaling," The Journal of Immunology, 2005, 174, 5351-5357.

Clever, J. et al., "RNA Secondary Structure and Binding Sites for gag Gene Products in the 5' Packaging Signal of Human Immunodeficiency Virus Type 1." J. of Virology (1995); 69(4): 2101-2109.

Cooper, Laurence JN, et al. "T-cell clones can be rendered specific for CD19: Toward the selective augmentation of the graft-versus-B-lineage leukemia effect." Blood (2003); 101.4: 1637-1644.

Cribbs et al., "Simplified production and concentration of lentiviral vectors to achieve high transduction in primary human T cells," BMC Biotechnol. Nov. 12, 2013;13:98.

Cullen, B.R., "Human Immunodeficiency Virus as a Prototypic Complex Retrovirus", Journal of Virology (1991); 65(3): 1053-1056.

Cullen et al., "Regulatory Pathways Governing HIV-1 Replication", Cell (1989); 58: 423-426.

Daudi et al., "Expression and immune responses to MAGE antigens predict survival in epithelial ovarian cancer," PLoS One. Aug. 7, 2014;9(8):e104099.

De Felipe et al., "Targeting of proteins derived from self-processing polyproteins containing multiple signal sequences." Traffic (2004); 5.8: 616-626.

(56)          References Cited

OTHER PUBLICATIONS

Desjarlais et al., "Use of a zinc-finger consensus sequence framework and specificity rules to design specific DNA binding proteins." Proceedings of the National Academy of Sciences (1993); 90.6: 2256-2260.

Desjarlais et al., "Length-encoded multiplex binding site determination: application to zinc finger proteins," Proceedings of the National Academy of Sciences (1994); 91.23: 11099-11103.

Donnelly, M. et al., "The 'cleavage' activities of foot-and-mouth disease virus 2A site-directed mutants and naturally occurring '2A-like' sequences." J Gen Virol. (2001); 82 (Pt 5): 1027-1041.

Duffour et al., "A MAGE-A4 peptide presented by HLA-A2 is recognized by cytolytic T lymphocytes," Eur. J. Immunol. Oct. 1999; 29(10):3329-37.

Duke et al., Sequence and structural elements that contribute to efficient encephalomyocarditis virus RNA translation, J Virol. Mar. 1992;66(3):1602-9.

Dull et al., "A third-generation lentivirus vector with a conditional packaging system", Journal of Virology (1998); 72(11): 8463-8671.

Engels et al., "Relapse or eradication of cancer is predicted by peptide-major histocompatibility complex affinity," Cancer Cell. Apr. 15, 2013;23(4):516-26.

Extended European Search Report mailed on Mar. 30, 2020, for European Application No. 17872043.9, 12 pages.

Flynn et al., "Stem memory T cells (TSCM)-their role in cancer and HIV immunotherapies," Clin Transl Immunology. Jul. 18, 2014;3(7):e20.

Fukuo, "Interleukin 2, IL-2," The Journal of Japan Atherosclerosis Society, 1996, 24, 4-5, 155-161.

Gattinoni et al., "A human memory T cell subset with stem cell-like properties," Nat Med. Sep. 18, 2011;17(10):1290-1297.

Giudicelli et al., "IMGT/LIGM-DB, the IMGT comprehensive database of immunoglobulin and T cell receptor nucleotide sequences," Nucleic Acids Res. Jan. 1, 2006;34(Database issue):D781-4.

Gure et al., "Cancer-testis genes are coordinately expressed and are markers of poor outcome in non-small cell lung cancer," Clin Cancer Res. Nov. 15, 2005;11(22):8055-62.

International Search Report and Written Opinion mailed on Apr. 3, 2018, for International Application No. PCT/US2017/062358, 15 pages.

International Search Report and Written Opinion mailed on Jul. 7, 2020, for International Application No. PCT/EP2020/058779, 12 pages.

International Search Report and Written Opinion mailed on Oct. 14, 2020, for International Application No. PCT/US2020/031796, 12 pages.

Haga-Friedman et al., "Incorporation of transmembrane hydrophobic mutations in the TCR enhance its surface expression and T cell functional avidity," J Immunol. Jun. 1, 2012;188(11):5538-46.

Huang et al., "Role of the hepatitis B virus posttranscriptional regulatory element in export of intronless transcripts," Molecular and Cellular Biology (1995); 15(7): 3864-3869.

Huez et al., "Two independent internal ribosome entry sites are involved in translation initiation of vascular endothelial growth factor mRNA," Mol Cell Biol. Nov. 1998;18(11):6178-90.

Irion, S. et al., "Identification and targeting of the ROSA26 locus in human embryonic stem cells", Nat Biotechnol. (2007); 25(12):1477-1482.

Jackson, et al., "The novel mechanism of initiation of picornavirus RNA translation", Trends Biochem Sci. (1990); 15(12): 477-483.

Jackson, et al., "Internal initiation of translation in eukaryotes: the picornavirus paradigm and beyond", RNA. (1995); 1(10): 985-1000.

Jena et al., "Driving CAR-Based T-Cell Therapy to Success," Curr Hematol Malig Rep. Mar. 2014; 9(1): 50-56.

Kageyama et al., "Adoptive Transfer of MAGE-A4 T-cell Receptor Gene-Transduced Lymphocytes in Patients with Recurrent Esophageal Cancer," Clin Cancer Res. May 15, 2015;21(10):2268-77.

Kim, Yang-Gyun, et al. "Hybrid restriction enzymes: zinc finger fusions to Fok I cleavage domain." Proceedings of the National Academy of Sciences (1996); 93.3: 1156-1160.

Kim et al., "Pattern of cancer/testis antigen expression in lung cancer patients," Int J Mol Med. Apr. 2012;29(4):656-62.

Kutner, et al., "Simplified production andconcentration of HIV-1-based lentiviral vectors using HYPERFlask vessels and anion exchange membrane chromatography", BMC Biotechnol. (2009); 9:10. p. 1-7.

Kutner et al., "Production, concentration and titration of pseudotyped HIV-1-based lentiviral vectors", Nature Protocols (2009); 4: 495-505.

Li et al., "Expression Profile of Cancer-Testis Genes in 121 Human Colorectal Cancer Tissue and Adjacent Normal Tissue," Clin Cancer Res (2005) 11 (5): 1809-1814.

Linette et al., "Cardiovascular toxicity and titin cross-reactivity of affinity-enhanced T cells in myeloma and melanoma," Blood. Aug. 8, 2013;122(6):863-71.

Liu et al., "Design of polydactyl zinc-finger proteins for unique addressing within complex genomes," Proceedings of the National Academy of Sciences (1997); 94.11: 5525-5530.

Liu et al., "HnRNP L binds a cis-acting RNA sequence element that enables intron-dependent gene expression," Genes & Dev. (1995); 9: 1766-1780.

Liu, X. et al. (2016). "A chimeric switch-receptor targeting PD1 augments the efficacy of second-generation CAR T cells in advanced solid tumors," Cancer Res. 76:1578-1590.

Lugli et al., "Identification, isolation and in vitro expansion of human and nonhuman primate T stem cell memory cells," Nat Protoc. Jan. 2013;8(1):33-42.

Maratea et al., "Deletion and fusion analysis of the phage phi X174 lysis gene E," Gene. 1985;40(1):39-46.

Morgan et al., "Cancer regression and neurological toxicity following anti-MAGE-A3 TCR gene therapy," J Immunother. Feb. 2013;36(2):133-51.

Murphy et al., "Genetic construction, expression, and melanoma-selective cytotoxicity of a diphtheria toxin-related alpha-melanocyte-stimulating hormone fusion protein," Proc Natl Acad Sci USA. Nov. 1986;83(21):8258-62.

Naldini L. et al., "Efficient transfer, integration, and sustained long-term expression of the transgene in adult rat brains injected with a lentiviral vector", Proc Natl Acad Sci USA (1996); 93(21): 11382-11388.

Naldini, L. et al., "In vivo gene delivery and stable transduction of nondividing cells by a lentiviral vector", Science (1996); 272(5259): 263-267.

Naldini, L., "Lentiviruses as gene transfer agents for delivery to non-dividing cells", Curr Opin Biotechnol. (1998); 5: 457-463.

Office Action issued by the Japanese Patent Office for Application No. 2019-526305, dated Oct. 4, 2021, 9 pages.

Office Action for Japanese Application No. JP20190526305 dated Jul. 4, 2022, 10 pages.

Otte et al., "MAGE—A gene expression pattern in primary breast cancer," Cancer Res. Sep. 15, 2001;61(18):6682-6687.

Ozaki et al., "Cytokine and Cytokine Receptor Pleiotropy and Redundancy," The Journal of Biological Chemistry, Aug. 16, 2002, 277,33, 29355-29358.

Patel, S. et al., "Impact of chimeric immune receptor extracellular protein domains on T cell function." Gene Ther (1999); 6(3): 412-419.

Pomerantz, et al., "Structure-based design of transcription factors." Science (1995); 267.5194: 93-96.

Pomerantz, et al., "Analysis of homeodomain function by structure-based design of a transcription factor," Proc Natl Acad Sci U S A. Oct. 10, 1995;92(21):9752-6.

Riddell et al., "Adoptive therapy with chimeric antigen receptor-modified T cells of defined subset composition," Cancer J. Mar.-Apr. 2014;20(2):141-4.

Ryan, M. et al., "Virus-encoded proteinases of the picornavirus super-group." J Gen Virol. (1997); 78 (Pt 4): 699-723.

Schmitt et al., T cell receptor gene therapy for cancer. Hum Gene Ther. Nov. 2009;20(11):1240-1248.

Shi et al., "Chimeric antigen receptor for adoptive immunotherapy of cancer: latest research and future prospects," Molecular Cancer 2014, 13:219, 8 pages.

(56) References Cited

OTHER PUBLICATIONS

Sommermeyer et al., "Minimal Amino Acid Exchange in Human TCR Constant Regions Fosters Improved Function of TCR Gene-Modified T Cells," The Journal of Immunology Jun. 1, 2010, 184 (11) 6223-6231.

Szymczak, Andrea L., et al. "Correction of multi-gene deficiency in vivo using a single'self-cleaving'2A peptide-based retroviral vector." Nature Biotechnology (2004); 22.5: 589-594.

Tajima et al., "Expression of cancer/testis (CT) antigens in lung cancer," Lung Cancer. Oct. 2003;42(1):23-33.

Takara Bio Inc., Idenshidonyujikken handobukku (handbook of gene transfer experimentation), Nov. 2015, p. 1-10.

Third Party Submission Under 37 CFR 1.290 submitted on Sep. 1, 2020, for U.S. Appl. No. 16/348,450, 9 pages.

Wang, Z., et al., "Detection of RNA Interference (RNAi) Mediated mRNA Cleavage in Fresh Injected Tumor Tissue from Patients in a Phase I Trial of pbi-shRNA™ Lipoplex Targeting Stathmin-1," Molecular Therapy, May 2014, vol. 22, Supplement 1, pp. S298-S299.

Xue et al., "Exploiting T cell receptor genes for cancer immunotherapy," Clin Exp Immunol. Feb. 2005;139(2):167-72.

Yamada et al., "Preferential expression of cancer/testis genes in cancer stem-like cells: proposal of a novel sub-category, cancer/testis/stem gene," Tissue Antigens. Jun. 2013;81(6):428-34.

Yang, S. et al., "Development of optimal bicistronic lentiviral vectors facilitates high-level TCR gene expression and robust tumor cell recognition", Gene Therapy, Nov. 2008, vol. 15, No. 21, pp. 1411-1423.

Zennou et al., "HIV-1 genome nuclear import is mediated by a central DNA flap," Cell. Apr. 14, 2000;101(2):173-85.

Zhang, C. et al. (2017). "Engineering CAR-T cells," Biomaker Res. 5:22, 6 total pages.

Zufferey et al., "Multiply attenuated lentiviral vector achieves efficient gene delivery in vivo", Nat Biotechnol. (1997), 15(9): 871-875.

Zufferey, R. et al., "Woodchuck hepatitis virus posttranscriptional regulatory element enhances expression of transgenes delivered by retroviral vectors." J Virol. (1999); 73(4): 2886-2892.

International Preliminary Report on Patentability for International Application No. PCT/EP20/58779 dated Sep. 28, 2021.

International Preliminary Report on Patentability for International Application No. PCT/US2017/062358 dated May 21, 2019.

International Preliminary Report on Patentability for International Application No. PCT/US2020/031796 dated Nov. 2, 2021.

Kim et al., "High Cleavage Efficiency of a 2A Peptide Derived from Porcine Teschovirus-1 in Human Cell Lines, Zebrafish and Mice", PLoS ONE, vol. 6 (4) e18556, (2011).

Watanabe et al., "Conferring CAR T Cells With Resistance to TGFbeta1 Using a Signal Converter," Molecular Therapy, May 2014, vol. 22, Supplement 1, pp. S298-S299.

Zhu et al., "A Pivotal Role for the Transmembrane Domain in Transforming Growth Factor-b Receptor Activation", The Journal of Biological Chemistry, vol. 274, No. 17, Issue of Apr. 23, pp. 11773-11781, (1999).

Supplementary European Search Report for EP Application No. 20802730.0 dated Jul. 11, 2023, 6 pages.

Extended European Search Report for EP Application No. 23216595.1 dated May 29, 2024.

Wang et al., "Detection of RNA Interference (RNAi) Mediated mRNA Cleavage in Fresh Injected Tumor Tissue from Patients in a Phase I Trial of pbi-shRNA (TM) Lipoplex Targeting Stathmin-1", Molecular Therapy. vol. 22. Nature Publishing Group, (2014).

* cited by examiner

SEQUENCE LISTING

```
<160> NUMBER OF SEQ ID NOS: 45

<210> SEQ ID NO 1
<211> LENGTH: 10
<212> TYPE: PRT
<213> ORGANISM: Homo sapiens

<400> SEQUENCE: 1

Gly Val Tyr Asp Gly Arg Glu His Thr Val
1               5                   10
```

-continued

```
<210> SEQ ID NO 2
<211> LENGTH: 277
<212> TYPE: PRT
<213> ORGANISM: Homo sapiens

<400> SEQUENCE: 2

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Ser Gly Gly Tyr Thr Gly Gly Phe Lys Thr Ile Phe Gly Ala
            115                 120                 125

Gly Thr Arg Leu Phe Val Lys Ala Asn Ile Gln Asn Pro Asp Pro Ala
            130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
                180                 185                 190

Phe Lys Ser Asn Ser Ala Val Ala Trp Ser Asn Lys Ser Asp Phe Ala
                195                 200                 205

Cys Ala Asn Ala Phe Asn Asn Ser Ile Ile Pro Glu Asp Thr Phe Phe
            210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 3
<211> LENGTH: 310
<212> TYPE: PRT
<213> ORGANISM: Homo sapiens

<400> SEQUENCE: 3

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45
```

-continued

```
Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
                100                 105                 110

Ser Gly Gly Asp Gly Asp Glu Gln Phe Phe Gly Pro Gly Thr Arg Leu
                115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
                195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
    275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 4
<211> LENGTH: 613
<212> TYPE: PRT
<213> ORGANISM: Artificial Sequence
<220> FEATURE:
<223> OTHER INFORMATION: Made in Lab - Fusion protein

<400> SEQUENCE: 4

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
                20                  25                  30

Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95
```

```
Leu Ser Ser Leu Glu Leu Gly Asp Ser Ala Leu Tyr Phe Cys Ala Ser
            100                 105                 110

Ser Gly Gly Asp Gly Asp Glu Gln Phe Phe Gly Pro Gly Thr Arg Leu
            115                 120                 125

Thr Val Leu Glu Asp Leu Lys Asn Val Phe Pro Pro Glu Val Ala Val
            130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
            210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
            290                 295                 300

Arg Lys Asp Ser Arg Gly Arg Ala Lys Arg Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ser Leu Ser Ser Leu Leu Lys Val Val Thr Ala Ser Leu Trp Leu
            340                 345                 350

Gly Pro Gly Ile Ala Gln Lys Ile Thr Gln Thr Gln Pro Gly Met Phe
            355                 360                 365

Val Gln Glu Lys Glu Ala Val Thr Leu Asp Cys Thr Tyr Asp Thr Ser
            370                 375                 380

Asp Pro Ser Tyr Gly Leu Phe Trp Tyr Lys Gln Pro Ser Ser Gly Glu
385                 390                 395                 400

Met Ile Phe Leu Ile Tyr Gln Gly Ser Tyr Asp Gln Gln Asn Ala Thr
                405                 410                 415

Glu Gly Arg Tyr Ser Leu Asn Phe Gln Lys Ala Arg Lys Ser Ala Asn
                420                 425                 430

Leu Val Ile Ser Ala Ser Gln Leu Gly Asp Ser Ala Met Tyr Phe Cys
            435                 440                 445

Ala Met Ser Gly Gly Tyr Thr Gly Gly Phe Lys Thr Ile Phe Gly Ala
            450                 455                 460

Gly Thr Arg Leu Phe Val Lys Ala Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
            500                 505                 510
```

-continued

```
Asp Val Tyr Ile Thr Asp Lys Thr Val Leu Asp Met Arg Ser Met Asp
        515                 520                 525

Phe Lys Ser Asn Ser Ala Val Ala Trp Ser Asn Lys Ser Asp Phe Ala
        530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
                580                 585                 590

Arg Ile Leu Leu Leu Lys Val Ala Gly Phe Asn Leu Leu Met Thr Leu
        595                 600                 605

Arg Leu Trp Ser Ser
        610
```

```
<210> SEQ ID NO 5
<211> LENGTH: 277
<212> TYPE: PRT
<213> ORGANISM: Artificial Sequence
<220> FEATURE:
<223> OTHER INFORMATION: Made in Lab - synthetic construct

<400> SEQUENCE: 5
```

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
                20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
        50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
                100                 105                 110

Ala Met Ser Gly Gly Tyr Thr Gly Gly Phe Lys Thr Ile Phe Gly Ala
        115                 120                 125

Gly Thr Arg Leu Phe Val Lys Ala Asn Ile Gln Asn Pro Asp Pro Ala
        130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
                180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
        210                 215                 220

Pro Ser Ser Asp Val Pro Cys Asp Val Lys Leu Val Glu Lys Ser Phe
225                 230                 235                 240

Glu Thr Asp Thr Asn Leu Asn Phe Gln Asn Leu Leu Val Ile Val Leu
                245                 250                 255
```

-continued

```
Arg Ile Leu Leu Leu Lys Val Ala Gly Phe Asn Leu Leu Met Thr Leu
            260                 265                 270

Arg Leu Trp Ser Ser
        275

<210> SEQ ID NO 6
<211> LENGTH: 310
<212> TYPE: PRT
<213> ORGANISM: Artificial Sequence
<220> FEATURE:
<223> OTHER INFORMATION: Made in Lab - synthetic construct

<400> SEQUENCE: 6

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
            85                  90                  95

Leu Ser Ser Leu Glu Leu Gly Asp Ser Ala Leu Tyr Phe Cys Ala Ser
            100                 105                 110

Ser Gly Gly Asp Gly Asp Glu Gln Phe Phe Gly Pro Gly Thr Arg Leu
            115                 120                 125

Thr Val Leu Glu Asp Leu Lys Asn Val Phe Pro Pro Glu Val Ala Val
            130                 135                 140

Phe Glu Pro Ser Lys Ala Glu Ile Ala His Thr Gln Lys Ala Thr Leu
145                 150                 155                 160

Val Cys Leu Ala Thr Gly Phe Tyr Pro Asp His Val Glu Leu Ser Trp
            165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
            245                 250                 255

Trp Gly Arg Ala Asp Cys Gly Ile Thr Ser Ala Ser Tyr His Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 7
<211> LENGTH: 613
```

<212> TYPE: PRT
<213> ORGANISM: Artificial Sequence
<220> FEATURE:
<223> OTHER INFORMATION: Made in Lab - fusion protein

<400> SEQUENCE: 7

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Gly Gly Asp Gly Asp Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Lys Ala Glu Ile Ala His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Ile Thr Ser Ala Ser Tyr His Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly Arg Ala Lys Arg Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ser Leu Ser Ser Leu Leu Lys Val Val Thr Ala Ser Leu Trp Leu
            340                 345                 350

Gly Pro Gly Ile Ala Gln Lys Ile Thr Gln Thr Gln Pro Gly Met Phe
        355                 360                 365

Val Gln Glu Lys Glu Ala Val Thr Leu Asp Cys Thr Tyr Asp Thr Ser
    370                 375                 380
```

-continued

```
Asp Pro Ser Tyr Gly Leu Phe Trp Tyr Lys Gln Pro Ser Ser Gly Glu
385                 390                 395                 400

Met Ile Phe Leu Ile Tyr Gln Gly Ser Tyr Asp Gln Gln Asn Ala Thr
                    405                 410                 415

Glu Gly Arg Tyr Ser Leu Asn Phe Gln Lys Ala Arg Lys Ser Ala Asn
                420                 425                 430

Leu Val Ile Ser Ala Ser Gln Leu Gly Asp Ser Ala Met Tyr Phe Cys
                435                 440                 445

Ala Met Ser Gly Gly Tyr Thr Gly Gly Phe Lys Thr Ile Phe Gly Ala
            450                 455                 460

Gly Thr Arg Leu Phe Val Lys Ala Asn Ile Gln Asn Pro Asp Pro Ala
465                 470                 475                 480

Val Tyr Gln Leu Arg Asp Ser Lys Ser Ser Asp Lys Ser Val Cys Leu
                    485                 490                 495

Phe Thr Asp Phe Asp Ser Gln Thr Asn Val Ser Gln Ser Lys Asp Ser
                500                 505                 510

Asp Val Tyr Ile Thr Asp Lys Thr Val Leu Asp Met Arg Ser Met Asp
                515                 520                 525

Phe Lys Ser Asn Ser Ala Val Ala Trp Ser Asn Lys Ser Asp Phe Ala
            530                 535                 540

Cys Ala Asn Ala Phe Asn Asn Ser Ile Ile Pro Glu Asp Thr Phe Phe
545                 550                 555                 560

Pro Ser Ser Asp Val Pro Cys Asp Val Lys Leu Val Glu Lys Ser Phe
                565                 570                 575

Glu Thr Asp Thr Asn Leu Asn Phe Gln Asn Leu Leu Val Ile Val Leu
                580                 585                 590

Arg Ile Leu Leu Leu Lys Val Ala Gly Phe Asn Leu Leu Met Thr Leu
            595                 600                 605

Arg Leu Trp Ser Ser
            610

<210> SEQ ID NO 8
<211> LENGTH: 671
<212> TYPE: PRT
<213> ORGANISM: Artificial Sequence
<220> FEATURE:
<223> OTHER INFORMATION: Made in Lab - synthetic construct

<400> SEQUENCE: 8

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125
```

```
Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Trp Met Ala Phe Val Ala Pro Ser Ile Cys
                165                 170                 175

Ile Ala Ile Ile Met Val Gly Ile Phe Ser Thr His Tyr Phe Gln Gln
                180                 185                 190

Lys Val Phe Val Leu Leu Ala Ala Leu Arg Pro Gln Trp Cys Ser Arg
        195                 200                 205

Glu Ile Pro Asp Pro Ala Asn Ser Thr Cys Ala Lys Lys Tyr Pro Ile
    210                 215                 220

Ala Glu Glu Lys Thr Gln Leu Pro Leu Asp Arg Leu Leu Ile Asp Trp
225                 230                 235                 240

Pro Thr Pro Glu Asp Pro Glu Pro Leu Val Ile Ser Glu Val Leu His
                245                 250                 255

Gln Val Thr Pro Val Phe Arg His Pro Pro Cys Ser Asn Trp Pro Gln
                260                 265                 270

Arg Glu Lys Gly Ile Gln Gly His Gln Ala Ser Glu Lys Asp Met Met
        275                 280                 285

His Ser Ala Ser Ser Pro Pro Pro Arg Ala Leu Gln Ala Glu Ser
    290                 295                 300

Arg Gln Leu Val Asp Leu Tyr Lys Val Leu Glu Ser Arg Gly Ser Asp
305                 310                 315                 320

Pro Lys Pro Glu Asn Pro Ala Cys Pro Trp Thr Val Leu Pro Ala Gly
                325                 330                 335

Asp Leu Pro Thr His Asp Gly Tyr Leu Pro Ser Asn Ile Asp Asp Leu
                340                 345                 350

Pro Ser His Glu Ala Pro Leu Ala Asp Ser Leu Glu Glu Leu Glu Pro
        355                 360                 365

Gln His Ile Ser Leu Ser Val Phe Pro Ser Ser Ser Leu His Pro Leu
    370                 375                 380

Thr Phe Ser Cys Gly Asp Lys Leu Thr Leu Asp Gln Leu Lys Met Arg
385                 390                 395                 400

Cys Asp Ser Leu Met Leu Gly Ser Gly Ala Thr Asn Phe Ser Leu Leu
                405                 410                 415

Lys Gln Ala Gly Asp Val Glu Glu Asn Pro Gly Pro Met Glu Ala Ala
        420                 425                 430

Val Ala Ala Pro Arg Pro Arg Leu Leu Leu Leu Val Leu Ala Ala Ala
        435                 440                 445

Ala Ala Ala Ala Ala Ala Leu Leu Pro Gly Ala Thr Ala Leu Gln Cys
    450                 455                 460

Phe Cys His Leu Cys Thr Lys Asp Asn Phe Thr Cys Val Thr Asp Gly
465                 470                 475                 480

Leu Cys Phe Val Ser Val Thr Glu Thr Thr Asp Lys Val Ile His Asn
                485                 490                 495

Ser Met Cys Ile Ala Glu Ile Asp Leu Ile Pro Arg Asp Arg Pro Phe
                500                 505                 510

Val Cys Ala Pro Ser Ser Lys Thr Gly Ser Val Thr Thr Thr Tyr Cys
        515                 520                 525

Cys Asn Gln Asp His Cys Asn Lys Ile Glu Leu Pro Thr Thr Val Lys
    530                 535                 540

Ser Ser Pro Gly Leu Gly Pro Val Glu Leu Trp Leu Ile Phe Phe Ala
```

-continued

```
545             550             555             560

Ser Leu Gly Ser Phe Leu Ser Ile Leu Leu Val Gly Val Leu Gly Tyr
                565             570             575

Leu Gly Leu Asn Arg Ala Ala Arg His Leu Cys Pro Pro Leu Pro Thr
            580             585             590

Pro Cys Ala Ser Ser Ala Ile Glu Phe Pro Gly Gly Lys Glu Thr Trp
            595             600             605

Gln Trp Ile Asn Pro Val Asp Phe Gln Glu Glu Ala Ser Leu Gln Glu
        610             615             620

Ala Leu Val Val Glu Met Ser Trp Asp Lys Gly Glu Arg Thr Glu Pro
625             630             635             640

Leu Glu Lys Thr Glu Leu Pro Glu Gly Ala Pro Glu Leu Ala Leu Asp
                645             650             655

Thr Glu Leu Ser Leu Glu Asp Gly Asp Arg Cys Lys Ala Lys Met
            660             665             670

<210> SEQ ID NO 9
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 9

Asp Gly Gly Gly Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 10

Thr Gly Glu Lys Pro
1               5

<210> SEQ ID NO 11
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 11

Gly Gly Arg Arg
1

<210> SEQ ID NO 12
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 12

Gly Gly Gly Gly Ser
1               5

<210> SEQ ID NO 13
<211> LENGTH: 14
<212> TYPE: PRT
```

<213> ORGANISM: Artificial Sequence
<220> FEATURE:
<223> OTHER INFORMATION: Exemplary linker sequence

<400> SEQUENCE: 13

Glu Gly Lys Ser Ser Gly Ser Gly Ser Glu Ser Lys Val Asp
1               5                   10

<210> SEQ ID NO 14
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 14

Lys Glu Ser Gly Ser Val Ser Ser Glu Gln Leu Ala Gln Phe Arg Ser
1               5                   10                  15

Leu Asp

<210> SEQ ID NO 15
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 15

Gly Gly Arg Arg Gly Gly Gly Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 16

Leu Arg Gln Arg Asp Gly Glu Arg Pro
1               5

<210> SEQ ID NO 17
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 17

Leu Arg Gln Lys Asp Gly Gly Gly Ser Glu Arg Pro
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 18

Leu Arg Gln Lys Asp Gly Gly Gly Ser Gly Gly Gly Ser Glu Arg Pro
1               5                   10                  15

<210> SEQ ID NO 19
<211> LENGTH: 18

```
<212> TYPE: PRT
<213> ORGANISM: Artificial Sequence
<220> FEATURE:
<223> OTHER INFORMATION: Exemplary linker sequence

<400> SEQUENCE: 19

Gly Ser Thr Ser Gly Ser Gly Lys Pro Gly Ser Gly Glu Gly Ser Thr
1               5                   10                  15

Lys Gly

<210> SEQ ID NO 20
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 20

Glu Xaa Xaa Tyr Xaa Gln Xaa
1               5

<210> SEQ ID NO 21
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 21

Glu Asn Leu Tyr Phe Gln Gly
1               5

<210> SEQ ID NO 22
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 22

Glu Asn Leu Tyr Phe Gln Ser
1               5

<210> SEQ ID NO 23
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 23

Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 24
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 24

Ala Thr Asn Phe Ser Leu Leu Lys Gln Ala Gly Asp Val Glu Glu Asn
1               5                   10                  15

Pro Gly Pro

<210> SEQ ID NO 25
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 25

Leu Leu Lys Gln Ala Gly Asp Val Glu Glu Asn Pro Gly Pro
1               5                   10

<210> SEQ ID NO 26
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 26

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 27
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 27

Glu Gly Arg Gly Ser Leu Leu Thr Cys Gly Asp Val Glu Glu Asn Pro
1               5                   10                  15

Gly Pro

<210> SEQ ID NO 28
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 28

Leu Leu Thr Cys Gly Asp Val Glu Glu Asn Pro Gly Pro
1               5                   10

<210> SEQ ID NO 29
<211> LENGTH: 23
<212> TYPE: PRT
<213> ORGANISM: Artificial Sequence
<220> FEATURE:
<223> OTHER INFORMATION: Self-cleaving polypeptide comprising 2A site

```
<400> SEQUENCE: 29

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 30
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 30

Gln Cys Thr Asn Tyr Ala Leu Leu Lys Leu Ala Gly Asp Val Glu Ser
1               5                   10                  15

Asn Pro Gly Pro
            20

<210> SEQ ID NO 31
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 31

Leu Leu Lys Leu Ala Gly Asp Val Glu Ser Asn Pro Gly Pro
1               5                   10

<210> SEQ ID NO 32
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 32

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 33
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 33

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 34
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 34
```

-continued

```
Leu Leu Lys Leu Ala Gly Asp Val Glu Ser Asn Pro Gly Pro
1               5                   10

<210> SEQ ID NO 35
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 35

Leu Leu Asn Phe Asp Leu Leu Lys Leu Ala Gly Asp Val Glu Ser Asn
1               5                   10                  15

Pro Gly Pro

<210> SEQ ID NO 36
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 36

Thr Leu Asn Phe Asp Leu Leu Lys Leu Ala Gly Asp Val Glu Ser Asn
1               5                   10                  15

Pro Gly Pro

<210> SEQ ID NO 37
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 37

Leu Leu Lys Leu Ala Gly Asp Val Glu Ser Asn Pro Gly Pro
1               5                   10

<210> SEQ ID NO 38
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 38

Asn Phe Asp Leu Leu Lys Leu Ala Gly Asp Val Glu Ser Asn Pro Gly
1               5                   10                  15

Pro

<210> SEQ ID NO 39
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 39

Gln Leu Leu Asn Phe Asp Leu Leu Lys Leu Ala Gly Asp Val Glu Ser
1               5                   10                  15

Asn Pro Gly Pro
            20
```

-continued

```
<210> SEQ ID NO 40
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 40

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 41
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 41

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 42
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 42

Leu Asn Phe Asp Leu Leu Lys Leu Ala Gly Asp Val Glu Ser Asn Pro
1               5                   10                  15

Gly Pro

<210> SEQ ID NO 43
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 43

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 44
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 44

Glu Ala Arg His Lys Gln Lys Ile Val Ala Pro Val Lys Gln Thr Leu
```

-continued

```
1                5                  10                    15

Asn Phe Asp Leu Leu Lys Leu Ala Gly Asp Val Glu Ser Asn Pro Gly
                 20                    25                    30

Pro

<210> SEQ ID NO 45
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 45 gccrccatgg                                                          10
```

ENGINEERED T CELLS

CROSS REFERENCE TO RELATED APPLICATIONS

This application is a National Stage application under 35 U.S.C. § 371 of International Application No. PCT/US2020/031796, filed May 7, 2020, which claims the benefit under 35 U.S.C. § 119(e) of U.S. Provisional Application No. 62/845,311, filed May 8, 2019, which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_122_01WO_ST25. The text file is 37 KB, was created on May 6, 2020, and is being submitted electronically via EFS-Web, concurrent with the filing of the specification.

BACKGROUND

Technical Field

The present disclosure relates to improved adoptive cell therapies. More particularly, the disclosure relates to improved signaling molecules, cells, and methods of using the same.

BRIEF SUMMARY

The present disclosure generally relates, in part, to improved adoptive immunotherapies, and in particular embodiments, immune effector cells comprising: a polynucleotide encoding an αβTCR that binds MAGEA4, preferably a human pairing enhanced αβTCR that binds MAGEA4, preferably the MAGEA4 peptide GVYDGREHTV (SEQ ID NO: 1) presented by the HLA-A*02:01 encoded molecule; and a chimeric TGFβ receptor (CTBR), compositions, and methods of using the same.

In various embodiments, a cell comprises a first polynucleotide encoding an engineered αβ TCR that binds MAGEA4 (MAGEA4 TCR); and a second polynucleotide encoding a fusion polypeptide comprising: a first polypeptide comprising an extracellular TGFβ1-binding domain of TGFβR2, a transmembrane domain, and an immune receptor intracellular signaling domain; a polypeptide cleavage signal; and a second polypeptide comprising an extracellular TGFβ1-binding domain of TGFβR1, a transmembrane domain, and an immune receptor intracellular signaling domain.

In various embodiments, a cell comprises a first polynucleotide encoding a human pairing enhanced αβ TCR that binds MAGEA4 (MAGEA4 eTCR); and a second polynucleotide encoding a fusion polypeptide comprising: a first polypeptide comprising an extracellular TGFβ1-binding domain of TGFβR2, a transmembrane domain, and an immune receptor intracellular signaling domain; a polypeptide cleavage signal; and a second polypeptide comprising an extracellular TGFβ1-binding domain of TGFβR1, a transmembrane domain, and an immune receptor intracellular signaling domain.

In particular embodiments, the immune receptor intracellular signaling domain of the first polypeptide is isolated from a cytokine receptor, an interleukin receptor, a pattern recognition receptor, or a toll-like receptor.

In certain embodiments, the immune receptor intracellular signaling domain of the second polypeptide is isolated from a cytokine receptor, an interleukin receptor, a pattern recognition receptor, or a toll-like receptor.

In particular embodiments, the immune receptor intracellular signaling domain of the first polypeptide is an IL-12Rβ2 intracellular signaling domain and the immune receptor intracellular signaling domain of the second polypeptide is an IL-12Rβ1 intracellular signaling domain.

In various embodiments, the transmembrane domain of the first polypeptide comprises an IL-12Rβ2 transmembrane domain.

In further embodiments, the transmembrane domain of the second polypeptide comprises an IL-12Rβ1 transmembrane domain.

In some embodiments, the immune receptor intracellular signaling domain of the first polypeptide is an IL-12Rβ1 intracellular signaling domain and the immune receptor intracellular signaling domain of the second polypeptide is an IL-12Rβ2 intracellular signaling domain.

In various embodiments, the transmembrane domain of the first polypeptide comprises an IL-12Rβ1 transmembrane domain.

In certain embodiments, the transmembrane domain of the second polypeptide comprises an IL-12Rβ2 transmembrane domain.

In particular embodiments, the immune receptor intracellular signaling domain of the first polypeptide is an IL-7Rα intracellular signaling domain and the immune receptor intracellular signaling domain of the second polypeptide is an IL-2Rγ intracellular signaling domain.

In further embodiments, the transmembrane domain of the first polypeptide comprises an IL-7Rα transmembrane domain.

In additional embodiments, the transmembrane domain of the second polypeptide comprises an IL-2Rγ transmembrane domain.

In various embodiments, the immune receptor intracellular signaling domain of the first polypeptide is an IL-2Rγ intracellular signaling domain and the immune receptor intracellular signaling domain of the second polypeptide is an IL-7Rα intracellular signaling domain.

In some embodiments, the transmembrane domain of the first polypeptide comprises an IL-2Rγ transmembrane domain.

In particular embodiments, the transmembrane domain of the second polypeptide comprises an IL-7Rα transmembrane domain.

In certain embodiments, the immune receptor intracellular signaling domain of the first polypeptide is an IL-2Rβ intracellular signaling domain and the immune receptor intracellular signaling domain of the second polypeptide is an IL-2Rγ intracellular signaling domain.

In various embodiments, the transmembrane domain of the first polypeptide comprises an IL-2Rβ transmembrane domain.

In further embodiments, the transmembrane domain of the second polypeptide comprises an IL-2Rγ transmembrane domain.

In certain embodiments, the immune receptor intracellular signaling domain of the first polypeptide is an IL-2Rγ intracellular signaling domain and the immune receptor intracellular signaling domain of the second polypeptide is an IL-2Rβ intracellular signaling domain.

In particular embodiments, the transmembrane domain of the first polypeptide comprises an IL-2Rγ transmembrane domain.

In some embodiments, the transmembrane domain of the second polypeptide comprises an IL-2Rβ transmembrane domain.

In additional embodiments, the immune receptor intracellular signaling domain of the first polypeptide is an IL-21R intracellular signaling domain and the immune receptor intracellular signaling domain of the second polypeptide is an IL-2Rγ intracellular signaling domain.

In various embodiments, the transmembrane domain of the first polypeptide comprises an IL-21R transmembrane domain.

In certain embodiments, the transmembrane domain of the second polypeptide comprises an IL-2Rγ transmembrane domain.

In particular embodiments, the immune receptor intracellular signaling domain of the first polypeptide is an IL-2Rγ intracellular signaling domain and the immune receptor intracellular signaling domain of the second polypeptide is an IL-21R intracellular signaling domain.

In further embodiments, the transmembrane domain of the first polypeptide comprises an IL-2Rγ transmembrane domain.

In some embodiments, the transmembrane domain of the second polypeptide comprises an IL-21R transmembrane domain.

In additional embodiments, the immune receptor intracellular signaling domain of the first polypeptide is an IL-18R1 intracellular signaling domain and the immune receptor intracellular signaling domain of the second polypeptide is an IL-18RAP intracellular signaling domain.

In various embodiments, the transmembrane domain of the first polypeptide comprises an IL-18R1 transmembrane domain.

In various embodiments, the transmembrane domain of the second polypeptide comprises an IL-18RAP transmembrane domain.

In particular embodiments, the immune receptor intracellular signaling domain of the first polypeptide is an IL-18RAP intracellular signaling domain and the immune receptor intracellular signaling domain of the second polypeptide is an IL-18R1 intracellular signaling domain.

In particular embodiments, the transmembrane domain of the first polypeptide comprises an IL-18RAP transmembrane domain.

In further embodiments, the transmembrane domain of the second polypeptide comprises an IL-18R1 transmembrane domain.

In certain embodiments, the immune receptor intracellular signaling domain of the first polypeptide is an IL-1R1 intracellular signaling domain and the immune receptor intracellular signaling domain of the second polypeptide is an IL-1RAP intracellular signaling domain.

In various embodiments, the transmembrane domain of the first polypeptide comprises an IL-1R1 transmembrane domain.

In some embodiments, the transmembrane domain of the second polypeptide comprises an IL-1RAP transmembrane domain.

In various embodiments, the immune receptor intracellular signaling domain of the first polypeptide is an IL-1RAP intracellular signaling domain and the immune receptor intracellular signaling domain of the second polypeptide is an IL-1R1 intracellular signaling domain.

In some embodiments, the transmembrane domain of the first polypeptide comprises an IL-1RAP transmembrane domain.

In particular embodiments, the transmembrane domain of the second polypeptide comprises an IL-1R1 transmembrane domain.

In certain embodiments, the immune receptor intracellular signaling domain of the first polypeptide is an IL-1RAP intracellular signaling domain and the immune receptor intracellular signaling domain of the second polypeptide is an IL-1RL2 intracellular signaling domain.

In various embodiments, the transmembrane domain of the first polypeptide comprises an IL-1RAP transmembrane domain.

In additional embodiments, the transmembrane domain of the second polypeptide comprises an IL-1RL2 transmembrane domain.

In further embodiments, the immune receptor intracellular signaling domain of the first polypeptide is an IL-1RL2 intracellular signaling domain and the immune receptor intracellular signaling domain of the second polypeptide is an IL-1RAP intracellular signaling domain.

In various embodiments, the transmembrane domain of the first polypeptide comprises an IL-1RL2 transmembrane domain.

In particular embodiments, the transmembrane domain of the second polypeptide comprises an IL-1RAP transmembrane domain.

In additional embodiments, the immune receptor intracellular signaling domain of the first polypeptide is an IFNAR1 intracellular signaling domain and the immune receptor intracellular signaling domain of the second polypeptide is an IFNAR2 intracellular signaling domain.

In various embodiments, the transmembrane domain of the first polypeptide comprises an IFNAR1 transmembrane domain.

In certain embodiments, the transmembrane domain of the second polypeptide comprises an IFNAR2 transmembrane domain.

In particular embodiments, the immune receptor intracellular signaling domain of the first polypeptide is an IFNAR2 intracellular signaling domain and the immune receptor intracellular signaling domain of the second polypeptide is an IFNAR1 intracellular signaling domain.

In some embodiments, the transmembrane domain of the first polypeptide comprises an IFNAR2 transmembrane domain.

In various embodiments, the transmembrane domain of the second polypeptide comprises an IFNAR1 transmembrane domain.

In further embodiments, the immune receptor intracellular signaling domain of the first polypeptide is a TLR1 intracellular signaling domain and the immune receptor intracellular signaling domain of the second polypeptide is a TLR1 intracellular signaling domain.

In certain embodiments, the transmembrane domain of the first polypeptide comprises a TLR1 transmembrane domain.

In particular embodiments, the transmembrane domain of the second polypeptide comprises a TLR1 transmembrane domain.

In some embodiments, the immune receptor intracellular signaling domain of the first polypeptide is a TLR2 intracellular signaling domain and the immune receptor intracellular signaling domain of the second polypeptide is a TLR2 intracellular signaling domain.

In various embodiments, the transmembrane domain of the first polypeptide comprises a TLR2 transmembrane domain.

In additional embodiments, the transmembrane domain of the second polypeptide comprises a TLR2 transmembrane domain.

In various embodiments, the immune receptor intracellular signaling domain of the first polypeptide is a TLR3 intracellular signaling domain and the immune receptor intracellular signaling domain of the second polypeptide is a TLR3 intracellular signaling domain.

In certain embodiments, the transmembrane domain of the first polypeptide comprises a TLR3 transmembrane domain.

In particular embodiments, the transmembrane domain of the second polypeptide comprises a TLR3 transmembrane domain.

In further embodiments, the immune receptor intracellular signaling domain of the first polypeptide is a TLR4 intracellular signaling domain and the immune receptor intracellular signaling domain of the second polypeptide is a TLR4 intracellular signaling domain.

In various embodiments, the transmembrane domain of the first polypeptide comprises a TLR4 transmembrane domain.

In some embodiments, the transmembrane domain of the second polypeptide comprises a TLR4 transmembrane domain.

In various embodiments, the immune receptor intracellular signaling domain of the first polypeptide is a TLR5 intracellular signaling domain and the immune receptor intracellular signaling domain of the second polypeptide is a TLR5 intracellular signaling domain.

In particular embodiments, the transmembrane domain of the first polypeptide comprises a TLR5 transmembrane domain.

In additional embodiments, the transmembrane domain of the second polypeptide comprises a TLR5 transmembrane domain.

In various embodiments, the immune receptor intracellular signaling domain of the first polypeptide is a TLR6 intracellular signaling domain and the immune receptor intracellular signaling domain of the second polypeptide is a TLR6 intracellular signaling domain.

In various embodiments, the transmembrane domain of the first polypeptide comprises a TLR6 transmembrane domain.

In certain embodiments, the transmembrane domain of the second polypeptide comprises a TLR6 transmembrane domain.

In particular embodiments, the immune receptor intracellular signaling domain of the first polypeptide is a TLR7 intracellular signaling domain and the immune receptor intracellular signaling domain of the second polypeptide is a TLR7 intracellular signaling domain.

In various embodiments, the transmembrane domain of the first polypeptide comprises a TLR7 transmembrane domain.

In further embodiments, the transmembrane domain of the second polypeptide comprises a TLR7 transmembrane domain.

In some embodiments, the immune receptor intracellular signaling domain of the first polypeptide is a TLR8 intracellular signaling domain and the immune receptor intracellular signaling domain of the second polypeptide is a TLR8 intracellular signaling domain.

In additional embodiments, the transmembrane domain of the first polypeptide comprises a TLR8 transmembrane domain.

In various embodiments, the transmembrane domain of the second polypeptide comprises a TLR8 transmembrane domain.

In particular embodiments, the immune receptor intracellular signaling domain of the first polypeptide is a TLR9 intracellular signaling domain and the immune receptor intracellular signaling domain of the second polypeptide is a TLR9 intracellular signaling domain.

In particular embodiments, the transmembrane domain of the first polypeptide comprises a TLR9 transmembrane domain.

In certain embodiments, the transmembrane domain of the second polypeptide comprises a TLR9 transmembrane domain.

In various embodiments, the immune receptor intracellular signaling domain of the first polypeptide is a TLR10 intracellular signaling domain and the immune receptor intracellular signaling domain of the second polypeptide is a TLR10 intracellular signaling domain.

In some embodiments, the transmembrane domain of the first polypeptide comprises a TLR10 transmembrane domain.

In particular embodiments, the transmembrane domain of the second polypeptide comprises a TLR10 transmembrane domain.

In certain embodiments, the polypeptide cleavage signal is a viral self-cleaving polypeptide.

In various embodiments, the polypeptide cleavage signal is a viral self-cleaving 2A polypeptide.

In particular embodiments, the polypeptide cleavage signal is a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In various embodiments, the fusion polypeptide comprises an amino acid sequence set forth in SEQ ID NO: 5.

In various embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-12Rβ2 transmembrane domain; and an IL-12Rβ2 intracellular signaling domain; a viral self-cleaving 2A peptide; and a TGFβR1 polypeptide comprising an extracellular TGFβ1-binding domain of TGFβR1; an IL-12Rβ1 transmembrane domain, and an IL-12Rβ1 intracellular signaling domain.

In particular embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-12Rβ1 transmembrane domain; and an IL-12Rβ1 intracellular signaling domain; a viral self-cleaving 2A peptide; and a TGFβR1 polypeptide comprising an extracellular TGFβ1-binding domain of TGFβR1; an IL-12Rβ2 transmembrane domain, and an IL-12Rβ2 intracellular signaling domain.

In certain embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-7Rα transmembrane domain; and an IL-7Rα intracellular signaling domain; a viral self-cleaving 2A peptide; and a TGFβR1 polypeptide comprising an extracellular TGFβ1-binding domain of TGFβR1; an IL-2Rγ transmembrane domain, and an IL-2Rγ intracellular signaling domain.

In some embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-2Rγ transmembrane domain, and an IL-2Rγ intracellular signaling domain; a viral self-cleaving 2A peptide; and a TGFβR1 polypeptide comprising an extracellular TGFβ1-binding domain of TGFβR1; an IL-7Rα transmembrane domain; and an IL-7Rα intracellular signaling domain.

In additional embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-2Rβ transmembrane domain; and an IL-2Rβ intracellular signaling domain; a viral self-cleaving 2A peptide; and a TGFβR1 polypeptide comprising an extracellular TGFβ1-binding domain of TGFβR1; an IL-2Rγ transmembrane domain, and an IL-2Rγ intracellular signaling domain.

In further embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-2Rγ transmembrane domain; and an IL-2Rγ intracellular signaling domain; a viral self-cleaving 2A peptide; and a TGFβR1 polypeptide comprising an extracellular TGFβ1-binding domain of TGFβR1; an IL-2Rβ transmembrane domain, and an IL-2Rβ intracellular signaling domain.

In various embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-21R transmembrane domain; and an IL-21R intracellular signaling domain; a viral self-cleaving 2A peptide; and a TGFβR1 polypeptide comprising an extracellular TGFβ1-binding domain of TGFβR1; an IL-2Rγ transmembrane domain, and an IL-2Rγ intracellular signaling domain.

In certain embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-2Rγ transmembrane domain; and an IL-2Rγ intracellular signaling domain; a viral self-cleaving 2A peptide; and a TGFβR1 polypeptide comprising an extracellular TGFβ1-binding domain of TGFβR1; an IL-21R transmembrane domain, and an IL-21R intracellular signaling domain.

In particular embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-18R1 transmembrane domain; and an IL-18R1 intracellular signaling domain; a viral self-cleaving 2A peptide; and a TGFβR1 polypeptide comprising an extracellular TGFβ1-binding domain of TGFβR1; an IL-18RAP transmembrane domain, and an IL-18RAP intracellular signaling domain.

In various embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-18RAP transmembrane domain; and an IL-18RAP intracellular signaling domain; a viral self-cleaving 2A peptide; and a TGFβR1 polypeptide comprising an extracellular TGFβ1-binding domain of TGFβR1; an IL-18R1 transmembrane domain, and an IL-18R1 intracellular signaling domain.

In various embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-1R1 transmembrane domain; and an IL-1R1 intracellular signaling domain; a viral self-cleaving 2A peptide; and a TGFβR1 polypeptide comprising an extracellular TGFβ1-binding domain of TGFβR1; an IL-1RAP transmembrane domain, and an IL-1RAP intracellular signaling domain.

In further embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IL-1RAP transmembrane domain; and an IL-1RAP intracellular signaling domain; a viral self-cleaving 2A peptide; and a TGFβR1 polypeptide comprising an extracellular TGFβ1-binding domain of TGFβR1; an IL-1R1 transmembrane domain, and an IL-1R1 intracellular signaling domain.

In some embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IFNAR1 transmembrane domain; and an IFNAR1 intracellular signaling domain; a viral self-cleaving 2A peptide; and a TGFβR1 polypeptide comprising an extracellular TGFβ1-binding domain of TGFβR1; an IFNAR2 transmembrane domain, and an IFNAR2 intracellular signaling domain.

In some embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an IFNAR2 transmembrane domain; and an IFNAR2 intracellular signaling domain; a viral self-cleaving 2A peptide; and a TGFβR1 polypeptide comprising an extracellular TGFβ1-binding domain of TGFβR1; an IFNAR1 transmembrane domain, and an IFNAR1 intracellular signaling domain.

In various embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an TLR1 transmembrane domain; and an TLR1 intracellular signaling domain; a viral self-cleaving 2A peptide; and a TGFβR1 polypeptide comprising an extracellular TGFβ1-binding domain of TGFβR1; an TLR1 transmembrane domain, and an TLR1 intracellular signaling domain.

In various embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an TLR2 transmembrane domain; and an TLR2 intracellular signaling domain; a viral self-cleaving 2A peptide; and a TGFβR1 polypeptide comprising an extracellular TGFβ1-binding domain of TGFβR1; an TLR2 transmembrane domain, and an TLR2 intracellular signaling domain.

In further embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an TLR3 transmembrane domain; and an TLR3 intracellular signaling domain; a viral self-cleaving 2A peptide; and a TGFβR1 polypeptide comprising an extracellular TGFβ1-binding domain of TGFβR1; an TLR3 transmembrane domain, and an TLR3 intracellular signaling domain.

In certain embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an TLR4 transmembrane domain; and an TLR4 intracellular signaling domain; a viral self-cleaving 2A peptide; and a TGFβR1 polypeptide comprising an extracellular TGFβ1-binding domain of TGFβR1; an TLR4 transmembrane domain, and an TLR4 intracellular signaling domain.

In particular embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an TLR5 transmembrane domain; and an TLR5 intracellular signaling domain; a viral self-cleaving 2A peptide; and a TGFβR1 polypeptide comprising an extracellular TGFβ1-binding domain of TGFβR1; an TLR5 transmembrane domain, and an TLR5 intracellular signaling domain.

In some embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an TLR6 transmembrane domain; and an TLR6 intracellular signaling domain; a viral self-cleaving 2A peptide; and a TGFβR1 polypeptide comprising an extracellular TGFβ1-binding domain of TGFβR1; an TLR6 transmembrane domain, and an TLR6 intracellular signaling domain.

In additional embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an TLR7 transmembrane domain; and an TLR7 intracellular signaling domain; a viral self-cleaving 2A peptide; and a TGFβR1 polypeptide comprising an extracellular TGFβ1-binding domain of TGFβR1; an TLR7 transmembrane domain, and an TLR7 intracellular signaling domain.

In various embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an TLR8 transmembrane domain; and an TLR8 intracellular signaling domain; a viral self-cleaving 2A peptide; and a TGFβR1 polypeptide comprising an extracellular TGFβ1-binding domain of TGFβR1; an TLR8 transmembrane domain, and an TLR8 intracellular signaling domain.

In various embodiments, a cell comprises a first polynucleotide encoding a MAGEA4 TCR; and a second polynucleotide encoding a fusion polypeptide comprising: a TGFβR2 polypeptide comprising an extracellular TGFβ1- binding domain of TGFβR2, an TLR9 transmembrane domain; and an TLR9 intracellular signaling domain; a viral self-cleaving 2A peptide; and a TGFβR1 polypeptide comprising an extracellular TGFβ1-binding domain of TGFβR1; an TLR9 transmembrane domain, and an TLR9 intracellular signaling domain.

In various embodiments, a cell comprises a first polynucleotide encoding a MAGEA4 TCR; and a second polynucleotide encoding a fusion polypeptide comprising: a TGFβR2 polypeptide comprising an extracellular TGFβ1-binding domain of TGFβR2, an TLR10 transmembrane domain; and an TLR10 intracellular signaling domain; a viral self-cleaving 2A peptide; and a TGFβR1 polypeptide comprising an extracellular TGFβ1-binding domain of TGFβR1; an TLR10 transmembrane domain, and an TLR10 intracellular signaling domain.

In particular embodiments, the viral self-cleaving 2A polypeptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In various embodiments, the fusion polypeptide comprises an amino acid sequence set forth in SEQ ID NO: 5.

In further embodiments, the MAGEA4 TCR binds the peptide GVYDGREHTV presented by the HLA-A*02:01 encoded molecule.

In some embodiments, the MAGEA4 TCR comprises an alpha chain comprising an amino acid sequence set forth in SEQ ID NO: 2 and a beta chain comprising an amino acid sequence set forth in SEQ ID NO: 3.

In various embodiments, the MAGEA4 TCR comprises an alpha chain comprising an amino acid sequence set forth in SEQ ID NO: 5 and a beta chain comprising an amino acid sequence set forth in SEQ ID NO: 6.

In particular embodiments, the cell is a hematopoietic cell.

In additional embodiments, the cell is a T cell.

In certain embodiments, the cell is a CD3+, CD4+, and/or CD8+ cell.

In various embodiments, the cell is an immune effector cell.

In some embodiments, the cell is a cytotoxic T lymphocytes (CTLs), a tumor infiltrating lymphocytes (TILs), or a helper T cells.

In certain embodiments, the cell is a natural killer (NK) cell or natural killer T (NKT) cell.

In particular embodiments, the source of the cell is peripheral blood mononuclear cells, bone marrow, lymph nodes tissue, cord blood, thymus issue, tissue from a site of infection, ascites, pleural effusion, spleen tissue, or tumors.

In various embodiments, a composition comprises a cell expressing a MAGEA4 TCR and a fusion polypeptide contemplated herein.

In further embodiments, a pharmaceutical composition comprises a pharmaceutically acceptable carrier and a cell expressing a MAGEA4 TCR and a fusion polypeptide contemplated herein.

In certain embodiments, a method of treating a subject in need thereof comprises administering the subject an effective amount of a composition contemplated herein.

In various embodiments, a method of treating, preventing, or ameliorating at least one symptom of a cancer, infectious disease, autoimmune disease, inflammatory disease, and immunodeficiency, or condition associated therewith, comprises administering to the subject an effective amount of a composition contemplated herein.

In particular embodiments, method of treating a solid cancer comprises administering to the subject an effective amount of a composition contemplated herein.

In some embodiments, the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, or skin cancer.

In certain embodiments, the solid cancer is a pancreatic cancer, a lung cancer, or a breast cancer.

In particular embodiments, a method of treating a hematological malignancy comprises administering to the subject an effective amount of a composition contemplated herein.

In various embodiments, the hematological malignancy is a leukemia, lymphoma, or multiple myeloma.

BRIEF DESCRIPTION OF THE SEQUENCE IDENTIFIERS

Figure 1:
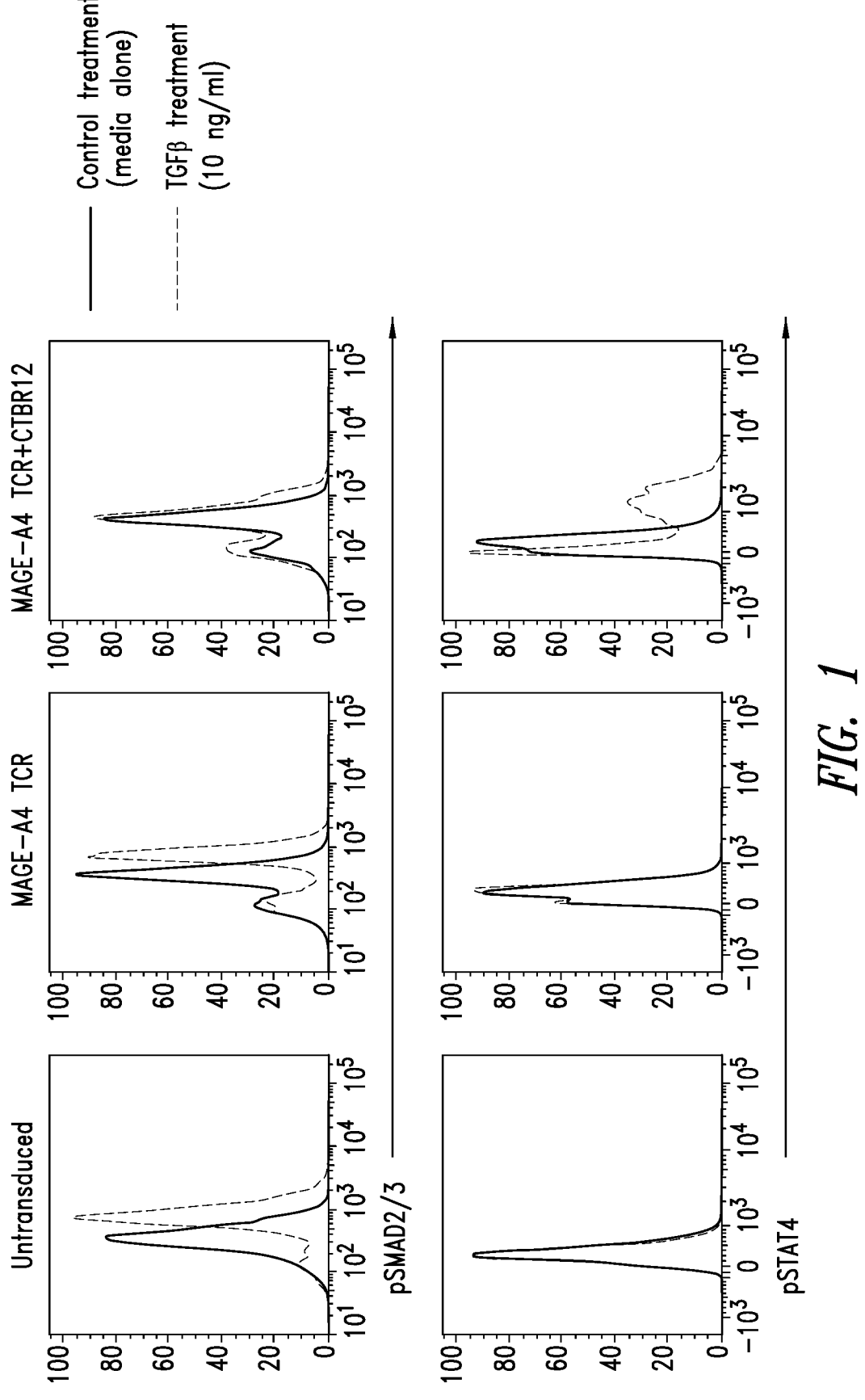
FIG. 1 shows STAT4 and SMAD2/3 phosphorylation in untransduced (UTD) T cells, T cells transduced with a LVV encoding a MAGEA4 TCR, and in T cells transduced with a LVV encoding a MAGEA4 TCR and a LVV encoding an IL-12 responsive chimeric TGFβ receptor (CTBR12), cultured in the presence or absence of TGFβ1 for 20 minutes.

SEQ ID NO: 1 sets forth the amino acid sequence of a MAGEA4 epitope.

SEQ ID NO: 2 sets forth the amino acid sequence of human MAGEA4 TCRα chain.

SEQ ID NO: 3 sets forth the amino acid sequence of human MAGEA4 TCRβ chain.

SEQ ID NO: 4 sets forth the amino acid sequence of human MAGEA4 TCR fusion polypeptide.

SEQ ID NO: 5 sets forth the amino acid sequence of human MAGEA4 eTCRα chain.

SEQ ID NO: 6 sets forth the amino acid sequence of human MAGEA4 eTCRβ chain.

SEQ ID NO: 7 sets forth the amino acid sequence of human MAGEA4 eTCR fusion polypeptide.

SEQ ID NO: 8 sets forth the amino acid sequence of an IL-12 responsive chimeric TGFβ receptor (CTBR12).

SEQ ID NO: 9-19 set for the amino acid sequence of various linkers.

SEQ ID NOs: 20-44 set for the amino acid sequence of protease cleavage sites and self-cleaving polypeptide cleavage sites.

SEQ ID NO: 45 sets forth the nucleotide sequence of a Kozak sequence.

In the foregoing sequences, X, if present, refers to any amino acid or the absence of an amino acid.

DETAILED DESCRIPTION

A. Overview

T cell receptor (TCR) expressing T cells have demonstrated limited, if any, efficacy in solid tumor indications, in part due to the immunosuppressive solid tumor microenvironment (TME). The overproduction of immunosuppressive cytokines, including TGFβ, by tumor cells and tumor-infiltrating lymphocytes contributes to an immunosuppressive tumor microenvironment. TGFβ inhibits T cell function via a variety of mechanisms. TGFβ is frequently associated with tumor metastasis and invasion, inhibiting the function of immune cells, and poor prognosis in patients with cancer. TGFβ signaling through TGFβR2 in tumor-specific CTLs dampens their function and frequency in the tumor, and blocking TGFβ signaling on CD8$^+$ T cells with monoclonal antibodies results in more rapid tumor surveillance and the presence of many more CTLs at the tumor site. To date, strategies to inhibit TGFβ in a clinical setting have not resulted in significant therapeutic benefits.

The present disclosure generally relates to immune effector cells that express MAGEA4 TCRs and polypeptides that convert an immunosuppressive TGFβ signal to an immunostimulatory signal and to cells expressing the polypeptides. Without wishing to be bound by any particular theory, the polypeptides contemplated herein are chimeric TGFβ receptors (CTBRs) that comprise the TGFβ binding domains of TGFβR1 and TGFβR2, that when linked to immunostimulatory endodomains and co-expressed in immune effector cells, can convert TGFβ exposure from an immunosuppressive signal to an immunostimulatory one that stimulates immune effector cell activity and function. Coexpression of chimeric TGFβ receptor polypeptides in immune effector cells renders the cells resistant to the immunosuppressive impacts of TGFβ, e.g., by restoring or increasing proinflammatory cytokine secretion. In particular preferred embodiments, the MAGEA4 TCR is a human MAGEA4 pairing enhanced TCR (eTCR) and the chimeric TGFβ receptor is CTBR12.

In various embodiments, the present disclosure contemplates, in part, immune effector cells that express a MAGEA4 TCR and CTBR polypeptides that convert an immunosuppressive TGFβ signal to an immunostimulatory signal mediated through or by one or more intracellular domains of one or more immune receptors.

In various embodiments, the present disclosure contemplates, in part, immune effector cells that express a MAGEA4 TCR and CTBR polypeptides that convert an immunosuppressive TGFβ signal to an immunostimulatory signal mediated through or by one or more intracellular domains of one or more cytokine receptors.

In various embodiments, the present disclosure contemplates, in part, immune effector cells that express a MAGEA4 TCR and CTBR polypeptides that convert an immunosuppressive TGFβ signal to an immunostimulatory signal mediated through or by one or more intracellular domains of one or more interleukin receptors.

In various embodiments, the present disclosure contemplates, in part, immune effector cells that express a MAGEA4 TCR and CTBR polypeptides that convert an immunosuppressive TGFβ signal to an immunostimulatory signal mediated through or by one or more intracellular domains of one or more pattern recognition receptors.

In various embodiments, the present disclosure contemplates, in part, immune effector cells that express a MAGEA4 TCR and CTBR polypeptides that convert an immunosuppressive TGFβ signal to an immunostimulatory signal mediated through or by one or more intracellular domains of one or more toll-like receptors.

In particular embodiments, the present disclosure contemplates, in part, immune effector cells that express a MAGEA4 TCR and a CTBR polypeptide comprising a TGFβR1 extracellular domain that binds TGFβ, a transmembrane domain and one or more intracellular domains of one or more immune receptors; and a CTBR polypeptide comprising a TGFβR2 extracellular domain that binds TGFβ, a transmembrane domain and one or more intracellular domains of one or more immune receptors. In one embodiment, the polypeptides are linked to each other by a polypeptide cleavage signal, e.g., a 2A polypeptide cleavage signal.

In particular embodiments, the present disclosure contemplates, in part, an immune effector cell, that expresses a MAGEA4 TCR (e.g., SEQ ID NOs: 2-4), preferably a MAGEA4 pairing enhanced TCR (eTCR; e.g., SEQ ID NOs: 5-7), preferably a MAGEA4 pairing enhanced TCR that binds the MAGEA4 peptide GVYDGREHTV presented by the HLA-A*02:01 encoded molecule, and a fusion polypeptide encoding a chimeric TGFβ receptor (CTBR) comprising a TGFβR1 extracellular domain that binds TGFβ, a transmembrane domain and one or more intracellular domains of one or more immune receptors; and a polypeptide comprising a TGFβR2 extracellular domain that binds TGFβ, a transmembrane domain and one or more intracellular domains of one or more immune receptors.

In particular embodiments, the transmembrane domains and intracellular signaling domains are isolated from an IL-12 receptor, an IL-7 receptor, an IL-15 receptor, an IL-21 receptor, an IL-2 receptor, an IL-1 receptor, an IL-18 receptor, an IL-36 receptor, a type I IFN receptor, a TLR1 receptor, a TLR2 receptor, a TLR3 receptor, a TLR4 receptor, a TLR5 receptor, a TLR6 receptor, a TLR7 receptor, a TLR8 receptor, a TLR9 receptor, or a TLR10 receptor.

In particular embodiments, the transmembrane domains and intracellular signaling domains are isolated from IL-12Rβ2, IL-7Rα, IL-2Rγ, IL-2Rβ, IL-21R, IL-18R1, IL-18RAP, IL-1R1, IL-1RAP, IFNAR1, IFNAR2, IL-1RL2, TLR1, TLR2, TLR3, TLR4, TLR5, TLR6, TLR7, TLR8, TLR9, or TLR10.

In preferred embodiments, the fusion polypeptide is an IL-12 responsive CTBR (CTBR12; e.g., SEQ ID NO: 8).

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual,* 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid The Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and CC Blackwell, eds., 1986); Roitt, *Essential Immunology*, 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as Advances in Immunology.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

An "antigen (Ag)" refers to a compound, composition, or substance that can stimulate the production of antibodies or a T cell response in an animal, including compositions (such as one that includes a cancer-specific protein) that are injected or absorbed into an animal. Exemplary antigens include but are not limited to lipids, carbohydrates, polysaccharides, glycoproteins, peptides, or nucleic acids. An antigen reacts with the products of specific humoral or cellular immunity, including those induced by heterologous antigens, such as the disclosed antigens.

A "target antigen" or "target antigen of interest" is an antigen that a binding domain contemplated herein, is designed to bind. In particular embodiments, the target antigen is selected from the group consisting of: alpha folate receptor, 5T4, αvβ6 integrin, BCMA, B7-H3, B7-H6, CAIX, CD16, CD19, CD20, CD22, CD30, CD33, CD37, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, STn, TAG72, TEMs, VEGFR2, and WT-1. In a preferred embodiment, the target antigen is MAGEA4.

MAGE-A4 belongs to the group of so-called Cancer/Testis antigens. Cancer/Testis antigens are expressed in various malignant tumors and germ cells but in no other adult tissues. Therefore, MAGE-A4 is an interesting immunotherapeutic target antigen. The human gene encoding MAGE-A4 is designated MAGEA4 (ENSG00000147381).

In one embodiment, the antigen is an MHC-peptide complex, such as a class I MHC-peptide complex or a class II MHC-peptide complex.

A "linker" refers to a plurality of amino acid residues between the various polypeptide domains, added for appropriate spacing and conformation of the molecule.

Illustrated examples of linkers suitable for use in particular embodiments contemplated herein include, but are not limited to the following amino acid sequences:

```
                                    (SEQ ID NO: 9)
GGG; DGGGS;

(SEQ ID NO: 10)
TGEKP (see, e.g., Liu et al.,
PNAS 5525-5530 (1997));

(SEQ ID NO: 11)
GGRR (Pomerantz et al. 1995, supra);

(SEQ ID NO: 12)
(GGGGS)_n wherein n = 1, 2, 3, 4 or 5
(Kim et al., PNAS 93, 1156-1160 (1996.);

(SEQ ID NO: 13)
EGKSSGSGSESKVD (Chaudhary etal.,
1990, Proc. Natl. Acad. Sci. U.S.A.
87:1066-1070);

(SEQ ID NO: 14)
KESGSVSSEQLAQFRSLD (Bird etal.,
1988, Science 242: 423-426), (SEQ ID NO: 15)
GGRRGGGS;

(SEQ ID NO: 16)
LRQRDGERP;

(SEQ ID NO: 17)
LRQKDGGGSERP;

(SEQ ID NO: 18)
LRQKD(GGGS)_2ERP.
```

Alternatively, flexible linkers can be rationally designed using a computer program capable of modeling both DNA-binding sites and the peptides themselves (Desjarlais & Berg, PNAS 90:2256-2260 (1993), PNAS 91:11099-11103 (1994) or by phage display methods. In one embodiment, the linker comprises the following amino acid sequence: GST-SGSGKPGSGEGSTKG (SEQ ID NO: 19) (Cooper et al., Blood, 101(4): 1637-1644 (2003)).

A "transmembrane domain" or "TM domain" is a domain that anchors a polypeptide to the plasma membrane of a cell. The TM domain may be derived either from a natural, synthetic, semi-synthetic, or recombinant source.

An "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

The term "effector function" or "effector cell function" refers to a specialized function of an immune effector cell. Effector function includes, but is not limited to, activation, cytokine production, proliferation and cytotoxic activity, including the release of cytotoxic factors, or other cellular responses elicited with antigen binding to the receptor expressed on the immune effector cell.

An "immune disorder" refers to a disease that evokes a response from the immune system. In particular embodiments, the term "immune disorder" refers to a cancer, an autoimmune disease, or an immunodeficiency. In one embodiment, immune disorders encompass infectious disease.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" refers to an individual cell of a cancerous growth or tissue. Cancer cells include both solid cancers and liquid cancers. A "tumor" or "tumor cell" refers generally to a swelling or lesion formed by an abnormal growth of cells, which may be benign, pre-malignant, or malignant. Most cancers form tumors, but liquid cancers, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

The term "relapse" refers to the diagnosis of return, or signs and symptoms of return, of a cancer after a period of improvement or remission.

"Remission," is also referred to as "clinical remission," and includes both partial and complete remission. In partial remission, some, but not all, signs and symptoms of cancer have disappeared. In complete remission, all signs and symptoms of cancer have disappeared, although cancer still may be in the body.

"Refractory" refers to a cancer that is resistant to, or non-responsive to, therapy with a particular therapeutic agent. A cancer can be refractory from the onset of treatment (i.e., non-responsive to initial exposure to the therapeutic agent), or as a result of developing resistance to the therapeutic agent, either over the course of a first treatment period or during a subsequent treatment period.

"Antigen negative" refers to a cell that does not express antigen or expresses a negligible amount of antigen that is undetectable. In one embodiment, antigen negative cells do not bind receptors directed to the antigen. In one embodiment, antigen negative cells do not substantially bind receptors directed to the antigen.

An "autoimmune disease" refers to a disease in which the body produces an immunogenic (i.e., immune system) response to some constituent of its own tissue. In other words, the immune system loses its ability to recognize some tissue or system within the body as "self" and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

An "immunodeficiency" means the state of a patient whose immune system has been compromised by disease or by administration of chemicals. This condition makes the system deficient in the number and type of blood cells needed to defend against a foreign substance. Immunodeficiency conditions or diseases are known in the art and include, for example, AIDS (acquired immunodeficiency syndrome), SCID (severe combined immunodeficiency disease), selective IgA deficiency, common variable immunodeficiency, X-linked agammaglobulinemia, chronic granulomatous disease, hyper-IgM syndrome, and diabetes.

An "infectious disease" refers to a disease that can be transmitted from person to person or from organism to organism, and is caused by a microbial or viral agent (e.g., common cold). Infectious diseases are known in the art and include, for example, hepatitis, sexually transmitted diseases (e.g., Chlamydia, gonorrhea), tuberculosis, HIV/AIDS, diphtheria, hepatitis B, hepatitis C, cholera, and influenza.

As used herein, the terms "individual" and "subject" are often used interchangeably and refer to any animal that exhibits a symptom of cancer or other immune disorder that can be treated with the compositions and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include human patients that have, have been diagnosed with, or are at risk or having, cancer or another immune disorder.

As used herein, the term "patient" refers to a subject that has been diagnosed with cancer or another immune disorder that can be treated with the compositions and methods disclosed elsewhere herein.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction of the disease or condition, or the delaying of the progression of the disease or condition, e.g., delaying tumor outgrowth. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

By "enhance" or "promote," or "increase" or "expand" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, persistence, cytokine secretion, and/or an increase in cancer cell killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a composition contemplated herein to produce, elicit, or cause a substantially similar or comparable physiological response (i.e., downstream effects) in a cell, as compared to the response caused by either vehicle, a control molecule/composition, or the response in a particular cell lineage. A comparable response is one that is not significantly different or measurable different from the reference response

C. MAGEA4 T Cell Receptors

MAGEA4 T cell receptors (TCRs) recognize a peptide fragment of MAGEA4 when it is presented by a major histocompatibility complex (MHC) molecule. There are two different classes of MHC molecules, MHC I and MHC II, that deliver peptides from different cellular compartments to the cell surface. Engagement of the TCR with antigen and MHC results in immune effector cell activation through a series of biochemical events mediated by associated enzymes, co-receptors, and specialized accessory molecules.

A TCR contemplated herein is a heterodimeric complex comprising a TCR alpha (TCRα) chain and a TCR beta (TCRβ) chain. The human TCRα locus is located on chromosome 14 (14q11.2). The mature TCRα chain comprises a variable domain derived from recombination of a variable (V) segment and a joining (J) segment, and a constant (C) domain. The human TCRβ locus is located on chromosome 7 (7q34). The mature TCRβ chain comprises a variable domain derived from recombination of a variable (V) segment, a diversity (D) segment, and a joining (J) segment, and one of two constant (C) domains.

In particular embodiments, the TCR binds MAGEA4.

In particular embodiments, the TCR is a human TCR that binds MAGEA4.

In preferred embodiments, the TCR is a human pairing enhanced TCR that binds MAGEA4.

Pairing enhanced MAGEA4 TCRs contemplated herein are engineered to increase TCR stability, TCR expression, specific TCR pairing and functional avidity.

In particular embodiments, the constant domains of the MAGEA4 TCRα and MAGEA4 TCRβ chains are engineered or modified to increase TCR stability, TCR expression, specific TCR pairing, and functional avidity.

To efficiently enhance correct pairing of the MAGEA4 TCR sequences and to avoid mispairing with endogenous TCR chains, the MAGEA4 pairing enhanced TCRs contemplated herein comprise minimally murinized TCRα and TCRβ constant domains and further comprise hydrophobic amino acid substitutions in the TCRα transmembrane domain.

In preferred embodiments, a MAGEA4 pairing enhanced TCR (eTCR) comprises a MAGEA4 TCRα chain that comprises a constant domain comprising minimal murinization amino acid substitutions at positions 90, 91, 92, and 93, and hydrophobic amino acid substitutions at positions 115, 118, and 119 of the constant region; and a MAGEA4 TCRβ chain that comprises a constant domain comprising minimal murinization amino acid substitutions at positions 18, 22, 133, 136, and 139.

In preferred embodiments, a MAGEA4 eTCR comprises a TCRα chain that comprises a constant domain comprising the following minimal murinization amino acid substitutions, P90S, E91D, S92V, and S93P and the following hydrophobic amino acid substitutions in the transmembrane domain of the constant region, S115L, G118V, and F119L; and a TCRβ chain that comprises a constant domain comprising the following minimal murinization amino acid substitutions, E18K, S22A, F133I, E/V136A, and Q139H.

In particular preferred embodiments, a MAGEA4 eTCR comprises a TCRα chain comprising the amino acid sequence set forth in SEQ ID NO: 5; and a TCRβ chain comprising the amino acid sequence set forth in SEQ ID NO: 6. In other particular preferred embodiments, the MAGEA4 eTCR is expressed as a fusion polypeptide comprising the amino acid sequence set forth in SEQ ID NO: 7.

D. Chimeric TGFβ Receptor (CTBR)

In particular embodiments, a cell comprising a polynucleotide encoding a human MAGEA4 TCR or a human MAGEA4 pairing enhanced TCR (eTCR) and a chimeric TGFβ receptor that transduces an immunostimulatory signal upon exposure to TGFβ, including but not limited to TGFβ1, is contemplated.

As used herein, the term "chimeric TGFβ receptor" refers to one or more non-naturally occurring polypeptides that converts TGFβ immunosuppressive signals from the tumor microenvironment to immunostimulatory signals in a T cell, e.g., stimulating immune effector cell activity and function, increasing production and/or secretion of proinflammatory cytokines. In particular embodiments, the term "chimeric TGFβ receptor" is used interchangeably with the term "CTBR."

In particular embodiments, the CTBR polypeptide comprises an extracellular TGFβ-binding domain of TGFβR2, a transmembrane domain, an intracellular signaling domain of an immune receptor including, but not limited to a cytokine receptor, an interleukin receptor, a pattern recognition receptor, and a toll-like receptor; a polypeptide cleavage signal; and an extracellular TGFβ-binding domain of TGFβR1, a transmembrane domain, and an intracellular signaling domain of an immune receptor including, but not limited to a cytokine receptor, an interleukin receptor, a pattern recognition receptor, and a toll-like receptor.

In particular embodiments, the CTBR is a fusion polypeptide that comprises a first polypeptide comprising an extracellular TGFβ-binding domain of TGFβR2, a transmembrane domain, an intracellular signaling domain of an immune receptor including, but not limited to a cytokine receptor, an interleukin receptor, a pattern recognition receptor, and a toll-like receptor; a polypeptide cleavage signal; and a second polypeptide comprising an extracellular TGFβ-binding domain of TGFβR1, a transmembrane domain, and an intracellular signaling domain of an immune receptor including, but not limited to a cytokine receptor, an interleukin receptor, a pattern recognition receptor, and a toll-like receptor.

In other particular embodiments, the CTBR is a complex of polypeptides comprising a polypeptide comprising an extracellular TGFβ-binding domain of TGFβR2, a transmembrane domain, and an intracellular signaling domain of an immune receptor including, but not limited to a cytokine receptor, an interleukin receptor, a pattern recognition receptor, and a toll-like receptor; and a polypeptide comprising an extracellular TGFβ-binding domain of TGFβR1, a transmembrane domain, and an intracellular signaling domain of an immune receptor including, but not limited to a cytokine receptor, an interleukin receptor, a pattern recognition receptor, and a toll-like receptor.

As used herein, the term "immune receptor" refers to a receptor that is expressed on the surface of an immune cell that modulates an immune response upon binding its cognate ligand. Immune receptors suitable for use in particular embodiments include, but are not limited to: cytokine receptors, interleukin receptors, pattern recognition receptors, and toll-like receptors, wherein signaling through the immune receptor stimulates an immune response.

Illustrative examples of immune receptor transmembrane and intracellular signaling domains that can be used in particular embodiments contemplated herein include, but are not limited to transmembrane and intracellular signaling domains isolated from an IL-12 receptor, an IL-7 receptor, an IL-15 receptor, an IL-21 receptor, an IL-2 receptor, an IL-1 receptor, an IL-18 receptor, an IL-36 receptor, a type I IFN receptor, a TLR1 receptor, a TLR2 receptor, a TLR3 receptor, a TLR4 receptor, a TLR5 receptor, a TLR6 receptor, a TLR7 receptor, a TLR8 receptor, a TLR9 receptor, or a TLR10 receptor.

Further illustrative examples of immune receptor transmembrane and intracellular signaling domains that can be used in particular embodiments contemplated herein include, but are not limited to transmembrane and intracellular signaling domains isolated from IL-12Rβ2, IL-7Rα, IL-2Rγ, IL-2Rβ, IL-21R, IL-18R1, IL-18RAP, IL-1R1, IL-1RAP, IFNAR1, IFNAR2, IL-1RL2, TLR1, TLR2, TLR3, TLR4, TLR5, TLR6, TLR7, TLR8, TLR9, or TLR10.

Illustrative examples of cytokine receptor transmembrane and intracellular signaling domains that can be used in particular embodiments contemplated herein include, but are not limited to transmembrane and intracellular signaling domains isolated from IL-12Rβ2, IL-7Rα, IL-2Rγ, IL-2Rβ, IL-21R, IL-18R1, IL-18RAP, IL-1R1, IL-1RAP, IFNAR1, IFNAR2, and IL-1RL2.

Illustrative examples of interleukin receptor transmembrane and intracellular signaling domains that can be used in particular embodiments contemplated herein include, but are not limited to transmembrane and intracellular signaling domains isolated from IL-12Rβ2, IL-7Rα, IL-2Rγ, IL-2Rβ, IL-21R, IL-18R1, IL-18RAP, IL-1R1, IL-1RAP, and IL-1RL2.

Illustrative examples of toll-like receptor transmembrane and intracellular signaling domains that can be used in particular embodiments contemplated herein include, but are not limited to transmembrane and intracellular signaling domains isolated from TLR1, TLR2, TLR3, TLR4, TLR5, TLR6, TLR7, TLR8, TLR9, and TLR10.

1. CTBR12 Polypeptides

Interleukin-12 (IL-12) is a cytokine that promotes T cell function and activity by, in part, increasing IFNγ expression, increasing T cell proliferation, and potentiating IL-12 signaling. IL-12 binds interleukin 12 receptor, beta 1 (IL-12Rβ1, also known as CD212) and interleukin 12 receptor, beta 2 (IL-12Rβ2).

IL-12 signaling through IL-12Rβ1 and IL-12Rβ2 results in STAT3, STAT4, and STAT5 phosphorylation. Phosphorylated STAT3/STAT4 translocates to the nucleus and binds the IFNγ promoter to increase IFNγ expression. Phosphorylated STAT4 also recruits Jun oncogene (c-Jun) to IFNγ promoter to increase IFNγ expression, and potentiates IL-12 signaling by increasing transcription of IL-12Rβ2. STAT5 phosphorylation increases T cell proliferation.

IL-12 signaling also increases expression of interleukin 2 receptor, alpha (IL-2R) by recruiting STAT4 and c-Jun to the promoter of IL-2R, thereby enhancing T cell proliferation.

In various embodiments, one or more immune effector cells, including immune effector cells expressing a MAGEA4 TCR or MAGEA4 eTCR, are modified by introducing one or more polynucleotides or vectors encoding one or more CTBR12 polypeptides. In various embodiments, one or more immune effector cells are modified by introducing one or more polynucleotides or vectors encoding a CTBR12 and a MAGEA4 TCR or MAGEA4 eTCR.

In particular embodiments, the CTBR12 converts an immunosuppressive TGFβ signal to an IL-12-mediated immunostimulatory signal. In particular embodiments a CTBR12 contemplated herein comprises: an extracellular TGFβ1-binding domain of TGFβR1, a transmembrane domain, and an IL-12Rβ1 intracellular signaling domain; a polypeptide cleavage signal; and an extracellular TGFβ1-binding domain of TGFβR2, a transmembrane domain, and an IL-12Rβ2 intracellular signaling domain. In particular embodiments a CTBR12 contemplated herein comprises: an extracellular TGFβ1-binding domain of TGFβR1, a transmembrane domain, and an IL-12Rβ2 intracellular signaling domain; a polypeptide cleavage signal; and an extracellular TGFβ1-binding domain of TGFβR2, a transmembrane domain, and an IL-12Rβ1 intracellular signaling domain.

In particular embodiments a CTBR12 contemplated herein comprises a fusion polypeptide comprising: a first polypeptide comprising an extracellular TGFβ1-binding domain of TGFβR1, a transmembrane domain, and an IL-12Rβ1 intracellular signaling domain; a polypeptide cleavage signal; and a second polypeptide comprising an extracellular TGFβ1-binding domain of TGFβR2, a transmembrane domain, and an IL-12R2 intracellular signaling domain. In particular embodiments a CTBR12 contemplated herein comprises a fusion polypeptide comprising: a first polypeptide comprising an extracellular TGFβ1-binding domain of TGFβR1, a transmembrane domain, and an IL-12R2 intracellular signaling domain; a polypeptide cleavage signal; and a second polypeptide comprising an extracellular TGFβ1-binding domain of TGFβR2, a transmembrane domain, and an IL-12Rβ1 intracellular signaling domain.

In particular embodiments, the CTBR12 is a complex of polypeptides comprising a first polypeptide comprising a polypeptide comprising an extracellular TGFβ1-binding domain of TGFβR1, a transmembrane domain, and an IL-12Rβ1 intracellular signaling domain; and a polypeptide comprising an extracellular TGFβ1-binding domain of TGFβR2, a transmembrane domain, and an IL-12Rβ2 intracellular signaling domain. In particular embodiments, the CTBR12 is a complex of polypeptides comprising a first polypeptide comprising a polypeptide comprising an extracellular TGFβ1-binding domain of TGFβR1, a transmembrane domain, and an IL-12Rβ2 intracellular signaling domain; and a polypeptide comprising an extracellular TGFβ1-binding domain of TGFβR2, a transmembrane domain, and an IL-12Rβ1 intracellular signaling domain.

In certain embodiments, a polypeptide comprises a transmembrane domain of TGFβR1 or TGFβR2. In certain embodiments, a polypeptide comprises a transmembrane domain of IL-12Rβ1 or IL-12Rβ2. In one embodiment, a polypeptide comprises an extracellular TGFβ1-binding domain of TGFβR1 and an IL-12Rβ1 transmembrane domain and intracellular signaling domain. In one embodiment, a polypeptide comprises an extracellular TGFβ1-binding domain of TGFβR2 and an IL-12Rβ2 transmembrane domain and intracellular signaling domain. In one embodiment, a polypeptide comprises an extracellular TGFβ1-binding domain of TGFβR1 and an IL-12Rβ2 transmembrane domain and intracellular signaling domain. In one embodiment, a polypeptide comprises an extracellular TGFβ1-binding domain of TGFβR2 and an IL-12Rβ1 transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

2. CTBR7 Polypeptides

Interleukin-7 (IL-7) is a cytokine that promotes T cell function and activity by, in part, improving T cell precursor survival and proliferation. IL-7 binds interleukin 7 receptor alpha (IL-7Rα, also known as CD127) and interleukin 2 receptor, common gamma chain (IL-2Rγ, also known as CD132 and γc). IL-7 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing a MAGEA4 TCR or MAGEA4 eTCR, are modified by introducing one or more polynucleotides or vectors encoding one or more CTBR7 polypeptides. In various embodiments, one or more immune effector cells are modified by introducing one or more polynucleotides or vectors encoding a CTBR7 and a MAGEA4 TCR or MAGEA4 eTCR.

In particular embodiments, the chimeric TGFβ receptor converts an immunosuppressive TGFβ signal to an IL-7-mediated immunostimulatory signal. In particular embodiments, a CTBR7 contemplated herein comprises: an extracellular TGFβ1-binding domain of TGFβR1, a transmembrane domain, and an IL-7Rα intracellular signaling domain; a polypeptide cleavage signal; and an extracellular TGFβ1-binding domain of TGFβR2, a transmembrane domain, and an IL-2Rγ intracellular signaling domain. In particular embodiments, a CTBR7 contemplated herein comprises: an extracellular TGFβ1-binding domain of TGFβR1, a transmembrane domain, and an IL-2Rγ intracellular signaling domain; a polypeptide cleavage signal; and an extracellular TGFβ1-binding domain of TGFβR2, a transmembrane domain, and an IL-7Rα intracellular signaling domain.

In particular embodiments a CTBR7 contemplated herein comprises a fusion polypeptide comprising: a first polypeptide comprising an extracellular TGFβ1-binding domain of TGFβR1, a transmembrane domain, and an IL-7Rα intracellular signaling domain; a polypeptide cleavage signal; and a second polypeptide comprising an extracellular TGFβ1-binding domain of TGFβR2, a transmembrane domain, and an IL-2Rγ intracellular signaling domain. In particular embodiments, a CTBR7 contemplated herein comprises a fusion polypeptide comprising: a first polypeptide comprising an extracellular TGFβ1-binding domain of TGFβR1, a transmembrane domain, and an IL-2Rγ intracellular signaling domain; a polypeptide cleavage signal; and a second polypeptide comprising an extracellular TGFβ1-binding domain of TGFβR2, a transmembrane domain, and an IL-7Rα intracellular signaling domain.

In particular embodiments, the CTBR7 is a complex of polypeptides comprising a first polypeptide comprising a polypeptide comprising an extracellular TGFβ1-binding domain of TGFβR1, a transmembrane domain, and an IL-7Rα intracellular signaling domain; and a polypeptide comprising an extracellular TGFβ1-binding domain of TGFβR2, a transmembrane domain, and an IL-2Rγ intracellular signaling domain. In particular embodiments, the CTBR7 is a complex of polypeptides comprising a first polypeptide comprising a polypeptide comprising an extracellular TGFβ1-binding domain of TGFβR1, a transmembrane domain, and an IL-2Rγ intracellular signaling domain; and a polypeptide comprising an extracellular TGFβ1-binding domain of TGFβR2, a transmembrane domain, and an IL-7Rα intracellular signaling domain.

In certain embodiments, a polypeptide comprises a transmembrane domain of TGFβR1 or TGFβR2. In certain embodiments, a polypeptide comprises a transmembrane domain of IL-7Rα or IL-2Rγ. In one embodiment, a polypeptide comprises an extracellular TGFβ1-binding domain of TGFβR1 and an IL-7Rα transmembrane domain and intracellular signaling domain. In one embodiment, a polypeptide comprises an extracellular TGFβ1-binding domain of TGFβR2 and an IL-2Rγ transmembrane domain and intracellular signaling domain. In one embodiment, a polypeptide comprises an extracellular TGFβ1-binding domain of TGFβR1 and an IL-2Rγ transmembrane domain and intracellular signaling domain. In one embodiment, a polypeptide comprises an extracellular TGFβ1-binding domain of TGFβR2 and an IL-7Rα transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

3. CTBR15 Polypeptides

Interleukin-15 (IL-15) is a cytokine that promotes T cell function and activity by, in part, improving T cell precursor survival and proliferation. IL-15 binds with high affinity to IL-15Rα (also known as CD215), which then associates with a complex comprising IL-2Rβ (also known as IL-15Rβ and CD122) and IL-2Rγ (also known as CD132 and γc), expressed either on the same cell (cis-presentation) or on a different cell (trans-presentation). IL-15 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing a MAGEA4 TCR or MAGEA4 eTCR, are modified by introducing one or more polynucleotides or vectors encoding one or more CTBR15 polypeptides, and optionally, a polynucleotide or vector encoding an IL-15Rα. In various embodiments, one or more immune effector cells are modified by introducing one or more polynucleotides or vectors encoding a CTBR15 and a MAGEA4 TCR or MAGEA4 eTCR, and optionally, a polynucleotide or vector encoding an IL-15Rα polypeptide.

In particular embodiments, the chimeric TGFβ receptor converts an immunosuppressive TGFβ signal to an IL-15-mediated immunostimulatory signal. In particular embodiments, a CTBR15 contemplated herein comprises: an extracellular TGFβ1-binding domain of TGFβR1, a transmembrane domain, and an IL-2Rβ intracellular signaling domain; a polypeptide cleavage signal; and an extracellular TGFβ1-binding domain of TGFβR2, a transmembrane domain, and an IL-2Rγ intracellular signaling domain. In particular embodiments, a CTBR15 contemplated herein comprises: an extracellular TGFβ1-binding domain of TGFβR1, a transmembrane domain, and an IL-2Rγ intracellular signaling domain; a polypeptide cleavage signal; and an extracellular TGFβ1-binding domain of TGFβR2, a transmembrane domain, and an IL-2Rβ intracellular signaling domain.

In particular embodiments a CTBR15 contemplated herein comprises a fusion polypeptide comprising: a first polypeptide comprising an extracellular TGFβ1-binding domain of TGFβR1, a transmembrane domain, and an IL-2Rβ intracellular signaling domain; a polypeptide cleavage signal; and a second polypeptide comprising an extracellular TGFβ1-binding domain of TGFβR2, a transmembrane domain, and an IL-2Rγ intracellular signaling domain. In particular embodiments, a CTBR15 contemplated herein comprises a fusion polypeptide comprising: a first polypeptide comprising an extracellular TGFβ1-binding domain of TGFβR1, a transmembrane domain, and an IL-2Rγ intracellular signaling domain; a polypeptide cleavage signal; and a second polypeptide comprising an extracellular TGFβ1-binding domain of TGFβR2, a transmembrane domain, and an IL-2Rβ intracellular signaling domain.

In particular embodiments, the CTBR15 is a complex of polypeptides comprising a first polypeptide comprising a polypeptide comprising an extracellular TGFβ1-binding domain of TGFβR1, a transmembrane domain, and an IL-2Rβ intracellular signaling domain; and a polypeptide comprising an extracellular TGFβ1-binding domain of TGFβR2, a transmembrane domain, and an IL-2Rγ intracellular signaling domain. In particular embodiments, the CTBR15 is a complex of polypeptides comprising a first polypeptide comprising a polypeptide comprising an extracellular TGFβ1-binding domain of TGFβR1, a transmembrane domain, and an IL-2Rγ intracellular signaling domain; and a polypeptide comprising an extracellular TGFβ1-binding domain of TGFβR2, a transmembrane domain, and an IL-2Rβ intracellular signaling domain.

In certain embodiments, a polypeptide comprises a transmembrane domain of TGFβR1 or TGFβR2. In certain embodiments, a polypeptide comprises a transmembrane domain of IL-2Rβ or IL-2Rγ. In one embodiment, a polypeptide comprises an extracellular TGFβ1-binding domain of TGFβR1 and an IL-2Rβ transmembrane domain and intracellular signaling domain. In one embodiment, a polypeptide comprises an extracellular TGFβ1-binding domain of TGFβR2 and an IL-2Rγ transmembrane domain and intracellular signaling domain. In one embodiment, a polypeptide comprises an extracellular TGFβ1-binding domain of TGFβR1 and an IL-2Rγ transmembrane domain and intracellular signaling domain. In one embodiment, a polypeptide comprises an extracellular TGFβ1-binding domain of TGFβR2 and an IL-2Rβ transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

4. CTBR21 Polypeptides

Interleukin-21 (IL-21) is a cytokine that promotes T cell function and activity by, in part, improving T cell precursor survival and proliferation. IL-21 binds to interleukin 21 receptor (IL-21R, also known as CD360) and IL-2Rγ (also known as CD132 and γc). IL-21 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing a MAGEA4 TCR or MAGEA4 eTCR, are modified by introducing one or more polynucleotides or vectors encoding one or more CTBR21 polypeptides. In various embodiments, one or more immune effector cells are modified by introducing one or more polynucleotides or vectors encoding a CTBR21 and a MAGEA4 TCR or MAGEA4 eTCR.

In particular embodiments, the chimeric TGFβ receptor converts an immunosuppressive TGFβ signal to an IL-21- mediated immunostimulatory signal. In particular embodiments, a CTBR21 contemplated herein comprises: an extracellular TGFβ1-binding domain of TGFβR1, a transmembrane domain, and an IL-21R intracellular signaling domain; a polypeptide cleavage signal; and an extracellular TGFβ1-binding domain of TGFβR2, a transmembrane domain, and an IL-2Rγ intracellular signaling domain. In particular embodiments, a CTBR21 contemplated herein comprises: an extracellular TGFβ1-binding domain of TGFβR1, a transmembrane domain, and an IL-2Rγ intracellular signaling domain; a polypeptide cleavage signal; and an extracellular TGFβ1-binding domain of TGFβR2, a transmembrane domain, and an IL-21R intracellular signaling domain.

In particular embodiments a CTBR21 contemplated herein comprises a fusion polypeptide comprising: a first polypeptide comprising an extracellular TGFβ1-binding domain of TGFβR1, a transmembrane domain, and an IL-21R intracellular signaling domain; a polypeptide cleavage signal; and a second polypeptide comprising an extracellular TGFβ1-binding domain of TGFβR2, a transmembrane domain, and an IL-2Rγ intracellular signaling domain. In particular embodiments, a CTBR21 contemplated herein comprises a fusion polypeptide comprising: a first polypeptide comprising an extracellular TGFβ1-binding domain of TGFβR1, a transmembrane domain, and an IL-2Rγ intracellular signaling domain; a polypeptide cleavage signal; and a second polypeptide comprising an extracellular TGFβ1-binding domain of TGFβR2, a transmembrane domain, and an IL-21R intracellular signaling domain.

In particular embodiments, the CTBR21 is a complex of polypeptides comprising a first polypeptide comprising a polypeptide comprising an extracellular TGFβ1-binding domain of TGFβR1, a transmembrane domain, and an IL-21R intracellular signaling domain; and a polypeptide comprising an extracellular TGFβ1-binding domain of TGFβR2, a transmembrane domain, and an IL-2Rγ intracellular signaling domain. In particular embodiments, the CTBR21 is a complex of polypeptides comprising a first polypeptide comprising a polypeptide comprising an extracellular TGFβ1-binding domain of TGFβR1, a transmembrane domain, and an IL-2Rγ intracellular signaling domain; and a polypeptide comprising an extracellular TGFβ1-binding domain of TGFβR2, a transmembrane domain, and an IL-21R intracellular signaling domain.

In certain embodiments, a polypeptide comprises a transmembrane domain of TGFβR1 or TGFβR2. In certain embodiments, a polypeptide comprises a transmembrane domain of IL-21R or IL-2Rγ. In one embodiment, a polypeptide comprises an extracellular TGFβ1-binding domain of TGFβR1 and an IL-21R transmembrane domain and intracellular signaling domain. In one embodiment, a polypeptide comprises an extracellular TGFβ1-binding domain of TGFβR2 and an IL-2Rγ transmembrane domain and intracellular signaling domain. In one embodiment, a polypeptide comprises an extracellular TGFβ1-binding domain of TGFβR1 and an IL-2Rγ transmembrane domain and intracellular signaling domain. In one embodiment, a polypeptide comprises an extracellular TGFβ1-binding domain of TGFβR2 and an IL-21R transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A)

peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

5. CTBR18 Polypeptides

Interleukin-18 (IL-18) is a cytokine that promotes T cell function and activity by, in part, increasing IFNγ expression, increasing T cell proliferation, and protecting against activation induced cell death (AICD). IL-18 binds interleukin 18 receptor 1, (IL-18R1, also known as CD218a) and interleukin 18 receptor accessory protein (IL-18RAP, CD218b).

IL-18 signaling through IL-18R1 and IL-18RAP results in activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase IFNγ expression and increase sensitivity to IL-12. The transcriptional program induced by IL-18 also increases T cell proliferation and protects against AICD.

In various embodiments, one or more immune effector cells, including immune effector cells expressing a MAGEA4 TCR or MAGEA4 eTCR, are modified by introducing one or more polynucleotides or vectors encoding one or more CTBR18 polypeptides. In various embodiments, one or more immune effector cells are modified by introducing one or more polynucleotides or vectors encoding a CTBR18 and a MAGEA4 TCR or MAGEA4 eTCR.

In particular embodiments, the chimeric TGFβ receptor converts an immunosuppressive TGFβ signal to an IL-18-mediated immunostimulatory signal. In particular embodiments, a CTBR18 contemplated herein comprises: an extracellular TGFβ1-binding domain of TGFβR1, a transmembrane domain, and an IL-18RAP intracellular signaling domain; a polypeptide cleavage signal; and an extracellular TGFβ1-binding domain of TGFβR2, a transmembrane domain, and an IL-18R1 intracellular signaling domain. In particular embodiments, a CTBR18 contemplated herein comprises: an extracellular TGFβ1-binding domain of TGFβR1, a transmembrane domain, and an IL-18R1 intracellular signaling domain; a polypeptide cleavage signal; and an extracellular TGFβ1-binding domain of TGFβR2, a transmembrane domain, and an IL-18RAP intracellular signaling domain.

In particular embodiments, a CTBR18 contemplated herein comprises a fusion polypeptide comprising: a first polypeptide comprising an extracellular TGFβ1-binding domain of TGFβR1, a transmembrane domain, and an IL-18R1 intracellular signaling domain; a polypeptide cleavage signal; and a second polypeptide comprising an extracellular TGFβ1-binding domain of TGFβR2, a transmembrane domain, and an IL-18RAP intracellular signaling domain. In particular embodiments, a CTBR18 contemplated herein comprises a fusion polypeptide comprising: a first polypeptide comprising an extracellular TGFβ1-binding domain of TGFβR1, a transmembrane domain, and an IL-18RAP intracellular signaling domain; a polypeptide cleavage signal; and a second polypeptide comprising an extracellular TGFβ1-binding domain of TGFβR2, a transmembrane domain, and an IL-18R1 intracellular signaling domain.

In particular embodiments, the CTBR18 is a complex of polypeptides comprising a first polypeptide comprising a polypeptide comprising an extracellular TGFβ1-binding domain of TGFβR1, a transmembrane domain, and an IL-18RAP intracellular signaling domain; and a polypeptide comprising an extracellular TGFβ1-binding domain of TGFβR2, a transmembrane domain, and an IL-18R1 intracellular signaling domain. In particular embodiments, the CTBR18 is a complex of polypeptides comprising a first polypeptide comprising a polypeptide comprising an extracellular TGFβ1-binding domain of TGFβR1, a transmembrane domain, and an IL-18R1 intracellular signaling domain; and a polypeptide comprising an extracellular TGFβ1-binding domain of TGFβR2, a transmembrane domain, and an IL-18RAP intracellular signaling domain.

In certain embodiments, a polypeptide comprises a transmembrane domain of TGFβR1 or TGFβR2. In certain embodiments, a polypeptide comprises a transmembrane domain of IL-18R1 or IL-18RAP. In one embodiment, a polypeptide comprises an extracellular TGFβ1-binding domain of TGFβR1 and an IL-18RAP transmembrane domain and intracellular signaling domain. In one embodiment, a polypeptide comprises an extracellular TGFβ1-binding domain of TGFβR2 and an IL-18R1 transmembrane domain and intracellular signaling domain. In one embodiment, a polypeptide comprises an extracellular TGFβ1-binding domain of TGFβR1 and an IL-18R1 transmembrane domain and intracellular signaling domain. In one embodiment, a polypeptide comprises an extracellular TGFβ1-binding domain of TGFβR2 and an IL-18RAP transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

6. CTBR1 Polypeptides

Interleukin-1 (IL-1) is a cytokine that promotes T cell function and activity by, in part, increasing IFNγ expression, increasing T cell proliferation, and potentiating protecting against activation induced cell death (AICD). IL-1 binds interleukin 1 receptor 1, (IL-1R1, also known as CD121a) and interleukin 1 receptor accessory protein (IL-1RAP).

IL-1 signaling through IL-1R1 and IL-1RAP results in activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase IFNγ expression and increase sensitivity to IL-12. The transcriptional program induced by IL-1 also increases T cell proliferation and protects against AICD.

In various embodiments, one or more immune effector cells, including immune effector cells expressing a MAGEA4 TCR or MAGEA4 eTCR, are modified by introducing one or more polynucleotides or vectors encoding one or more CTBR1 polypeptides. In various embodiments, one or more immune effector cells are modified by introducing one or more polynucleotides or vectors encoding a CTBR1 and a MAGEA4 TCR or MAGEA4 eTCR.

In particular embodiments, the chimeric TGFβ receptor converts an immunosuppressive TGFβ signal to an IL-1-mediated immunostimulatory signal. In particular embodiments, a CTBR1 contemplated herein comprises: an extracellular TGFβ1-binding domain of TGFβR1, a transmembrane domain, and an IL-1RAP intracellular signaling domain; a polypeptide cleavage signal; and an extracellular TGFβ1-binding domain of TGFβR2, a transmembrane domain, and an IL-1R1 intracellular signaling domain. In particular embodiments, a CTBR1 contemplated herein comprises: an extracellular TGFβ1-binding domain of TGFβR1, a transmembrane domain, and an IL-1R1 intracellular signaling domain; a polypeptide cleavage signal; and an extracellular TGFβ1-binding domain of TGFβR2, a transmembrane domain, and an IL-1RAP intracellular signaling domain.

In particular embodiments, a CTBR1 contemplated herein comprises a fusion polypeptide comprising: a first polypeptide comprising an extracellular TGFβ1-binding domain of TGFβR1, a transmembrane domain, and an IL-1R1 intracellular signaling domain; a polypeptide cleavage signal; and a second polypeptide comprising an extracellular TGFβ1-binding domain of TGFβR2, a transmembrane domain, and an IL-1RAP intracellular signaling domain. In particular embodiments, a CTBR1 contemplated herein comprises a fusion polypeptide comprising: a first polypeptide comprising an extracellular TGFβ1-binding domain of TGFβR1, a transmembrane domain, and an IL-1RAP intracellular signaling domain; a polypeptide cleavage signal; and a second polypeptide comprising an extracellular TGFβ1-binding domain of TGFβR2, a transmembrane domain, and an IL-1R1 intracellular signaling domain.

In particular embodiments, the CTBR1 is a complex of polypeptides comprising a first polypeptide comprising a polypeptide comprising an extracellular TGFβ1-binding domain of TGFβR1, a transmembrane domain, and an IL-1RAP intracellular signaling domain; and a polypeptide comprising an extracellular TGFβ1-binding domain of TGFβR2, a transmembrane domain, and an IL-1R1 intracellular signaling domain. In particular embodiments, the CTBR1 is a complex of polypeptides comprising a first polypeptide comprising a polypeptide comprising an extracellular TGFβ1-binding domain of TGFβR1, a transmembrane domain, and an IL-1R1 intracellular signaling domain; and a polypeptide comprising an extracellular TGFβ1-binding domain of TGFβR2, a transmembrane domain, and an IL-1RAP intracellular signaling domain.

In certain embodiments, a polypeptide comprises a transmembrane domain of TGFβR1 or TGFβR2. In certain embodiments, a polypeptide comprises a transmembrane domain of IL-1R1 or IL-1RAP. In one embodiment, a polypeptide comprises an extracellular TGFβ1-binding domain of TGFβR1 and an IL-1RAP transmembrane domain and intracellular signaling domain. In one embodiment, a polypeptide comprises an extracellular TGFβ1-binding domain of TGFβR2 and an IL-1R1 transmembrane domain and intracellular signaling domain. In one embodiment, a polypeptide comprises an extracellular TGFβ1-binding domain of TGFβR1 and an IL-1R1 transmembrane domain and intracellular signaling domain. In one embodiment, a polypeptide comprises an extracellular TGFβ1-binding domain of TGFβR2 and an IL-1RAP transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

7. CTBR.TLR Polypeptides

Toll like receptors (TLR1 through TLR10) are pattern recognition receptors that detect invading pathogens and activate the innate and adaptive immune responses. Activation of TLRs by various ligands leads to induction of a pro-inflammatory transcriptional program and expression of multiple inflammatory cytokines.

TLR signaling occurs via homodimerization of TLR signaling domains leading to activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase inflammatory cytokine production and induce proliferation. TLR activation can also lead to the activation of IRF3 and IRF7 transcription factors.

In various embodiments, one or more immune effector cells, including immune effector cells expressing a MAGEA4 TCR or MAGEA4 eTCR, are modified by introducing one or more polynucleotides or vectors encoding one or more CTBR.TLR polypeptides. In various embodiments, one or more immune effector cells are modified by introducing one or more polynucleotides or vectors encoding a CTBR.TLR and a MAGEA4 TCR or MAGEA4 eTCR.

In particular embodiments, the chimeric TGFβ receptor converts an immunosuppressive TGFβ signal to a TLR-mediated immunostimulatory signal. In particular embodiments, a CTBR.TLR contemplated herein comprises: an extracellular TGFβ1-binding domain of TGFβR1, a transmembrane domain, and a TLR intracellular signaling domain; a polypeptide cleavage signal; and an extracellular TGFβ1-binding domain of TGFβR2, a transmembrane domain, and an identical TLR signaling domain.

In particular embodiments, a CTBR.TLR contemplated herein comprises a fusion polypeptide comprising: a first polypeptide comprising an extracellular TGFβ1-binding domain of TGFβR1, a transmembrane domain, and a TLR intracellular signaling domain; a polypeptide cleavage signal; and a second polypeptide comprising an extracellular TGFβ1-binding domain of TGFβR2, a transmembrane domain, and an identical TLR signaling domain.

In particular embodiments, the CTBR.TLR is a complex of polypeptides comprising a first polypeptide comprising a polypeptide comprising an extracellular TGFβ1-binding domain of TGFβR1, a transmembrane domain, and a TLR intracellular signaling domain; and a polypeptide comprising an extracellular TGFβ1-binding domain of TGFβR2, a transmembrane domain, and an identical TLR intracellular signaling domain.

In certain embodiments, a polypeptide comprises a transmembrane domain of TGFβR1 or TGFβR2. In certain embodiments, a polypeptide comprises a transmembrane domain of a TLR. In one embodiment, a polypeptide comprises an extracellular TGFβ1-binding domain of TGFβR1 and a TLR transmembrane domain and intracellular signaling domain. In one embodiment, a polypeptide comprises an extracellular TGFβ1-binding domain of TGFβR2 and a TLR transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In one embodiment, the polypeptide cleavage signal is a P2A or T2A viral self-cleaving polypeptide.

E. Polypeptides

Various polypeptides are contemplated herein, including, but not limited to, MAGEA4 TCRs, MAGEA4 eTCRs, CTBRs, fusion proteins comprising the foregoing polypeptides and fragments thereof. "Polypeptide," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full length protein, or a fusion protein, and may include post-translational modifications of the polypeptide, for example, glycosylations, acetylations, phosphorylations and the like, as well as other modifications known in the art, both naturally occurring and non-naturally occurring.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of a polypeptide by introducing one or more substitutions, deletions, additions and/or insertions the polypeptide. In particular embodiments, polypeptides include polypeptides having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any of the reference sequences contemplated herein, typically where the variant maintains at least one biological activity of the reference sequence.

Polypeptides variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long.

In particular embodiments, the polypeptides set forth herein may comprise one or more amino acids denoted as "X." "X" if present in an amino acid SEQ ID NO, refers to any one or more amino acids. In particular embodiments, SEQ ID NOs denoting a fusion protein comprise a sequence of continuous X residues that cumulatively represent any amino acid sequence.

As noted above, polypeptides may be altered in various ways including amino acid substitutions, deletions, trunca-tions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., (*Molecular Biology of the Gene*, Fourth Edition, Benjamin/ Cummings, Menlo Park, Calif., 1987) and the references cited therein. Guidance as to appropriate amino acid substi-tutions that do not affect biological activity of the protein of interest may be found in the model of Dayhoff et al., (1978) *Atlas of Protein Sequence and Structure (Natl. Biomed. Res. Found*, Washington, D.C.).

In certain embodiments, a polypeptide variant comprises one or more conservative substitutions. A "conservative substitution" is one in which an amino acid is substituted for another amino acid that has similar properties, such that one skilled in the art of peptide chemistry would expect the secondary structure and hydropathic nature of the polypep-tide to be substantially unchanged. Modifications may be made in the structure of the polynucleotides and polypep-tides contemplated in particular embodiments and still obtain a functional molecule that encodes a variant or derivative polypeptide with desirable characteristics. When it is desired to alter the amino acid sequence of a polypeptide to create an equivalent, or even an improved, variant poly-peptide, one skilled in the art, for example, can change one or more of the codons of the encoding DNA sequence, e.g., according to Table 1.

TABLE 1

| Amino Acid Codons | | | | | | | |
|---|---|---|---|---|---|---|---|
| Amino Acids | One letter code | Three letter code | Codons | | | | |
| Alanine | A | Ala | GCA | GCC | GCG | GCU | |
| Cysteine | C | Cys | UGC | UGU | | | |
| Aspartic acid | D | Asp | GAC | GAU | | | |
| Glutamic acid | E | Glu | GAA | GAG | | | |
| Phenylalanine | F | Phe | UUC | UUU | | | |
| Glycine | G | Gly | GGA | GGC | GGG | GGU | |
| Histidine | H | His | CAC | CAU | | | |
| Isoleucine | I | Iso | AUA | AUC | AUU | | |
| Lysine | K | Lys | AAA | AAG | | | |
| Leucine | L | Leu | UUA | UUG | CUA | CUC | CUG | CUU |
| Methionine | M | Met | AUG | | | | |
| Asparagine | N | Asn | AAC | AAU | | | |
| Proline | P | Pro | CCA | CCC | CCG | CCU | |
| Glutamine | Q | Gln | CAA | CAG | | | |
| Arginine | R | Arg | AGA | AGG | CGA | CGC | CGG | CGU |
| Serine | S | Ser | AGU | AGU | UCA | UCC | UCG | UCU |
| Threonine | T | Thr | ACA | ACC | ACG | ACU | |
| Valine | V | Val | GUA | GUC | GUG | GUU | |
| Tryptophan | W | Trp | UGG | | | | |
| Tyrosine | Y | Tyr | UAC | UAU | | | |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, iso-leucine, proline, phenylalanine, methionine, tryptophan), and uncharged polar (glycine, asparagine, glutamine, cyste-ine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

In one embodiment, where expression of two or more polypeptides is desired, the polynucleotide sequences encoding them can be separated by an IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide seg-ments.

In another embodiment, two or more polypeptides can be expressed as a fusion protein that comprises one or more self-cleaving polypeptide sequences as disclosed elsewhere herein.

Fusion polypeptides can comprise one or more polypep-tide domains or segments including, but are not limited to signal peptides, cell permeable peptide domains (CPP), DNA binding domains, nuclease domains, etc., epitope tags (e.g., maltose binding protein ("MBP"), glutathione S trans-ferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subse-quences, and interspecies homologs, so long as the desired activity of the fusion polypeptide is preserved.

Fusion polypeptides may be produced by chemical syn-thetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise a linker that can be used to link the one or more polypeptides or domains within a polypeptide. A peptide linker sequence may be employed to separate any two or more polypeptide compo-nents by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26).

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus Ma proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 20), for example, ENLYFQG (SEQ ID NO: 21) and ENLYFQS (SEQ ID NO: 22), wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

Illustrative examples of 2A sites are provided in Table 2.

36

TABLE 2

| SEQ ID NO: 23 | GSGATNFSLLKQAGDVEENPGP |
| SEQ ID NO: 24 | ATNFSLLKQAGDVEENPGP |
| SEQ ID NO: 25 | LLKQAGDVEENPGP |
| SEQ ID NO: 26 | GSGEGRGSLLTCGDVEENPGP |
| SEQ ID NO: 27 | EGRGSLLTCGDVEENPGP |
| SEQ ID NO: 28 | LLTCGDVEENPGP |
| SEQ ID NO: 29 | GSGQCTNYALLKLAGDVESNPGP |
| SEQ ID NO: 30 | QCTNYALLKLAGDVESNPGP |
| SEQ ID NO: 31 | LLKLAGDVESNPGP |
| SEQ ID NO: 32 | GSGVKQTLNFDLLKLAGDVESNPGP |
| SEQ ID NO: 33 | VKQTLNFDLLKLAGDVESNPGP |
| SEQ ID NO: 34 | LLKLAGDVESNPGP |
| SEQ ID NO: 35 | LLNFDLLKLAGDVESNPGP |
| SEQ ID NO: 36 | TLNFDLLKLAGDVESNPGP |
| SEQ ID NO: 37 | LLKLAGDVESNPGP |
| SEQ ID NO: 38 | NFDLLKLAGDVESNPGP |
| SEQ ID NO: 39 | QLLNFDLLKLAGDVESNPGP |
| SEQ ID NO: 40 | APVKQTLNFDLLKLAGDVESNPGP |
| SEQ ID NO: 41 | VTELLYRMKRAETYCPRPLLAIHP TEARHKQKIVAPVKQT |
| SEQ ID NO: 42 | LNFDLLKLAGDVESNPGP |
| SEQ ID NO: 43 | LLAIHPTEARHKQKIVAPVKQTLN FDLLKLAGDVESNPGP |
| SEQ ID NO: 44 | EARHKQKIVAPVKQTLNFDLLKLA GDVESNPGP |

In preferred embodiments, a polypeptide comprises a MAGEA4 TCR, a MAGEA4 eTCR, or one or more CTBR polypeptides.

F. Polynucleotides

In particular embodiments, polynucleotides encoding MAGEA4 TCRs, CTBRs, engineered TCRs, fusion proteins comprising the foregoing polypeptides and fragments thereof are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

In various illustrative embodiments, polynucleotides contemplated herein include, but are not limited to polynucleotides encoding MAGEA4 TCRs, MAGEA4 eTCRs, one or more CTBR polypeptides, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc, 1994-1998, Chapter 15.

As used herein, "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man.

In various embodiments, a polynucleotide comprises an mRNA encoding a polypeptide contemplated herein. In certain embodiments, the mRNA comprises a cap, one or more nucleotides, and a poly(A) tail.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the premessenger (premRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In particular embodiments, the polynucleotides are codon optimized for expression and/or stability. Further, alleles of the genes comprising the polynucleotide sequences provided herein may also be used. Alleles are endogenous genes that are altered as a result of one or more mutations, such as deletions, additions and/or substitutions of nucleotides.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector.

Illustrative examples of vectors include, but are not limited to plasmid, autonomously replicating sequences, and transposable elements, e.g., Sleeping Beauty, PiggyBac.

Additional Illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) U3 promoter (Haas et al. *Journal of Virology.* 2003; 77(17): 9439-9450).

In one embodiment, a vector comprises an MNDU3 promoter.

In one embodiment, a vector comprises an EF1a promoter comprising the first intron of the human EF1a gene.

In one embodiment, a vector comprises an EF1a promoter that lacks the first intron of the human EF1a gene.

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

In a particular embodiment, it may be desirable to express a polynucleotide a T cell specific promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene*, 323:67), the cumate inducible gene switch (WO 2002/088346), tetracycline-dependent regulatory systems, etc. Inducer agents include, but are not limited to glucocorticoids, estrogens, mifepristone (RU486), metals, interferons, small molecules, cumate, tetracycline, doxycycline, and variants thereof.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. J. Virol 66(3): 1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO: 45), where R is a purine (A or G) (Kozak, 1986. *Cell.* 44(2):283-92, and Kozak, 1987. *Nucleic Acids Res.* 15(20): 8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), or another suitable heterologous or endogenous polyA sequence known in the art.

In some embodiments, a polynucleotide or cell harboring the polynucleotide utilizes a suicide gene, including an inducible suicide gene to reduce the risk of direct toxicity and/or uncontrolled proliferation. In specific embodiments, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In particular embodiments, one or more polynucleotides encoding a MAGEA4 TCRα chain and a TCRβ chain, including eTCR chains, and/or one or more CTBR polypeptides are introduced into a cell (e.g., an immune effector cell) by non-viral or viral vectors. The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to mRNA, plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy*. 10:180-187; and Balazs et al. (2011) *Journal of Drug Delivery*. 2011:1-12. Antibody-targeted, bacterially derived, non-living nanocell-based delivery is also contemplated in particular embodiments.

In various embodiments, the polynucleotide is an mRNA that is introduced into a cell in order to transiently express a desired polypeptide. As used herein, "transient" refers to expression of a non-integrated transgene for a period of hours, days or weeks, wherein the period of time of expression is less than the period of time for expression of the polynucleotide if integrated into the genome or contained within a stable plasmid replicon in the cell.

In particular embodiments, viral vectors are used to deliver one or more polynucleotides contemplated herein to a T cell.

Illustrative examples of viral vector systems suitable for use in particular embodiments contemplated herein include but are not limited to adeno-associated virus (AAV), retrovirus (including lentivirus), herpes simplex virus, adenovirus, and vaccinia virus vectors.

In particular embodiments, a polycistronic polynucleotide encoding a MAGEA4 TCR (SEQ ID NO: 4) comprising a TCRα chain (SEQ ID NO: 2) and a TCRβ chain (SEQ ID NO: 3) and a polycistronic polynucleotide encoding a CTBR (SEQ ID NO: 8) are introduced into a cell using non-viral or viral vectors. In particular embodiments, a polycistronic polynucleotide encoding a fusion protein encoding a MAGEA4 eTCR (SEQ ID NO: 7) comprising an eTCRα chain (SEQ ID NO: 5) and an eTCRβ chain (SEQ ID NO: 6) and a polycistronic polynucleotide encoding a CTBR (SEQ ID NO: 8) are introduced into a cell using non-viral or viral vectors.

In particular embodiments, a polycistronic polynucleotide encoding a MAGEA4 TCR (SEQ ID NO: 4) comprising a TCRα chain (SEQ ID NO: 2) and a TCRβ chain (SEQ ID NO: 3) and a CTBR (SEQ ID NO: 8) are introduced into a cell using a non-viral or viral vector. In particular embodiments, a polycistronic polynucleotide encoding a fusion protein encoding a MAGEA4 eTCR (SEQ ID NO: 7) comprising an eTCRα chain (SEQ ID NO: 5) and an eTCRβ chain (SEQ ID NO: 6) and a CTBR (SEQ ID NO: 8) are introduced into a cell using a non-viral or viral vector.

G. Genetically Modified Cells

In various embodiments, cells are modified to express a MAGEA4 TCR or MAGEA4 eTCR and CTBRs, for use in the treatment of cancer. Cells may be non-genetically modified to express the polypeptides contemplated herein, or in particular preferred embodiments, cells may be genetically modified to express the polypeptides contemplated herein. As used herein, the term "genetically engineered" or "genetically modified" refers to the addition of extra genetic material in the form of DNA or RNA into the total genetic material in a cell. The terms, "genetically modified cells,"

"modified cells," and "redirected cells," are used interchangeably in particular embodiments.

In particular embodiments, the MAGEA4 TCR and one or more CTBR polypeptides contemplated herein are introduced and expressed in immune effector cells to improve the resistance of the cells to the immunosuppressive signals in the TME mediated by TGFβ. In particular embodiments, MAGEA4 eTCR and one or more CTBR polypeptides are introduced and expressed in immune effector cells.

An "immune effector cell," is any cell of the immune system that has one or more effector functions (e.g., cytotoxic cell killing activity, secretion of cytokines, induction of ADCC and/or CDC). The illustrative immune effector cells contemplated herein are T lymphocytes, in particular cytotoxic T cells (CTLs; CD8+ T cells), TILs, and helper T cells (HTLs; CD4+ T cells. In one embodiment, immune effector cells include natural killer (NK) cells. In one embodiment, immune effector cells include natural killer T (NKT) cells. Immune effector cells can be autologous/autogeneic ("self") or non-autologous ("non-self," e.g., allogeneic, syngeneic or xenogeneic).

"Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are autologous.

Illustrative immune effector cells suitable for introducing CTBR polypeptides contemplated herein include T lymphocytes. The terms "T cell" or "T lymphocyte" are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4$^+$ T cell) CD4$^+$ T cell, a cytotoxic T cell (CTL; CD8$^+$ T cell), CD4$^+$CD8$^+$ T cell, CD4$^-$CD8$^-$ T cell, or any other subset of T cells. Other illustrative populations of T cells suitable for use in particular embodiments include naïve T cells and memory T cells.

As would be understood by the skilled person, other cells may also be used as immune effector cells with MAGEA4 TCR or MAGEA4 eTCR and one or more CTBR polypeptides contemplated herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro. Thus, in particular embodiments, immune effector cell includes progenitors of immune effectors cells such as hematopoietic stem cells (HSCs) contained within the CD34$^+$ population of cells derived from cord blood, bone marrow or mobilized peripheral blood which upon administration in a subject differentiate into mature immune effector cells, or which can be induced in vitro to differentiate into mature immune effector cells.

As used herein, immune effector cells genetically engineered to contain a specific chimeric receptor may be referred to as, "antigen specific redirected immune effector cells."

The term, "CD34$^+$ cell," as used herein refers to a cell expressing the CD34 protein on its cell surface. "CD34," as used herein refers to a cell surface glycoprotein (e.g., sialomucin protein) that often acts as a cell-cell adhesion factor and is involved in T cell entrance into lymph nodes.

The CD34+ cell population contains hematopoietic stem cells (HSC), which upon administration to a patient differentiate and contribute to all hematopoietic lineages, including T cells, NK cells, NKT cells, neutrophils and cells of the monocyte/macrophage lineage.

Methods for making the immune effector cells which express a MAGEA4 TCR or MAGEA4 eTCR and a chimeric TGFβ receptor polypeptide contemplated herein are provided in particular embodiments. In one embodiment, the method comprises transfecting or transducing immune effector cells isolated from an individual such that the immune effector cells express a MAGEA4 TCR or MAGEA4 eTCR and one or more chimeric TGFβ receptor polypeptides as contemplated herein. In one embodiment, the method comprises transfecting or transducing immune effector cells isolated from an individual such that the immune effector cells express a MAGEA4 TCR or MAGEA4 eTCR and one or more chimeric TGFβ receptor polypeptides and MAGEA4 TCRs or MAGEA4 eTCRs contemplated herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified. In this regard, the immune effector cells may be cultured before and/or after being genetically modified.

In particular embodiments, prior to in vitro manipulation or genetic modification of the immune effector cells described herein, the source of cells is obtained from a subject. In particular embodiments, the modified immune effector cells comprise T cells.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In other embodiments, an isolated or purified population of T cells is used. In some embodiments, after isolation of PBMC, both cytotoxic and helper T lymphocytes can be sorted into naïve, memory, and effector T cell subpopulations either before or after activation, expansion, and/or genetic modification.

In one embodiment, an isolated or purified population of T cells expresses one or more of the markers including, but not limited to a CD3+, CD4+, CD8+, or a combination thereof.

In certain embodiments, the T cells are isolated from an individual and first activated and stimulated to proliferate in vitro prior to being modified to express a chimeric TGFβ receptor polypeptide.

In order to achieve sufficient therapeutic doses of T cell compositions, T cells are often subjected to one or more rounds of stimulation, activation and/or expansion. T cells can be activated and expanded generally using methods as described, for example, in U.S. Pat. Nos. 6,352,694; 6,534, 055; 6,905,680; 6,692,964; 5,858,358; 6,887,466; 6,905, 681; 7,144,575; 7,067,318; 7,172,869; 7,232,566; 7,175, 843; 5,883,223; 6,905,874; 6,797,514; and 6,867,041, each of which is incorporated herein by reference in its entirety. In particular embodiments, T cells are activated and expanded for about 6 hours, about 12 hours, about 18 hours or about 24 hours prior to introduction of vectors or polynucleotides encoding the MAGEA4 TCR or MAGEA4 eTCR and the chimeric TGFβ receptor polypeptides.

In one embodiment, T cells are activated at the same time that they are modified.

In various embodiments, a method of generating an immune effector cell comprises activating a population of cells comprising T cells and expanding the population of T cells. T cell activation can be accomplished by providing a primary stimulation signal through the T cell TCR/CD3 complex and by providing a secondary costimulation signal through an accessory molecule, e.g., CD28.

The TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, and 64.1.

In addition to the primary stimulation signal provided through the TCR/CD3 complex, induction of T cell responses requires a second, costimulatory signal. In particular embodiments, a CD28 binding agent can be used to provide a costimulatory signal. Illustrative examples of CD28 binding agents include but are not limited to: natural CD 28 ligands, e.g., a natural ligand for CD28 (e.g., a member of the B7 family of proteins, such as B7-1 (CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10.

In one embodiment, the molecule providing the primary stimulation signal, for example a molecule which provides stimulation through the TCR/CD3 complex and the costimulatory molecule are coupled to the same surface.

In certain embodiments, binding agents that provide stimulatory and costimulatory signals are localized on the surface of a cell. This can be accomplished by transfecting or transducing a cell with a nucleic acid encoding the binding agent in a form suitable for its expression on the cell surface or alternatively by coupling a binding agent to the cell surface.

In another embodiment, the molecule providing the primary stimulation signal, for example a molecule which provides stimulation through the TCR/CD3 complex and the costimulatory molecule are displayed on antigen presenting cells.

In one embodiment, the molecule providing the primary stimulation signal, for example a molecule which provides stimulation through the TCR/CD3 complex and the costimulatory molecule are provided on separate surfaces.

In a certain embodiment, one of the binding agents that provides stimulatory and costimulatory signals is soluble (provided in solution) and the other agent(s) is provided on one or more surfaces.

In a particular embodiment, the binding agents that provide stimulatory and costimulatory signals are both provided in a soluble form (provided in solution).

In various embodiments, the methods for making T cells contemplated herein comprise activating T cells with anti-CD3 and anti-CD28 antibodies.

In one embodiment, expanding T cells activated by the methods contemplated herein further comprises culturing a population of cells comprising T cells for several hours (about 3 hours) to about 7 days to about 28 days or any hourly integer value in between. In another embodiment, the T cell composition may be cultured for 14 days. In a particular embodiment, T cells are cultured for about 21 days. In another embodiment, the T cell compositions are cultured for about 2-3 days. Several cycles of stimulation/ activation/expansion may also be desired such that culture time of T cells can be 60 days or more.

In particular embodiments, conditions appropriate for T cell culture include an appropriate media (e.g., Minimal Essential Media or RPMI Media 1640 or, X-vivo 15, (Lonza)) and one or more factors necessary for proliferation and viability including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α or any other additives suitable for the growth of cells known to the skilled artisan.

Further illustrative examples of cell culture media include, but are not limited to RPMI 1640, Clicks, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02).

In particular embodiments, PBMCs or isolated T cells are contacted with a stimulatory agent and costimulatory agent, such as anti-CD3 and anti-CD28 antibodies, generally attached to a bead or other surface, in a culture medium with appropriate cytokines, such as IL-2, IL-7, and/or IL-15.

In other embodiments, artificial APC (aAPC) made by engineering K562, U937, 721.221, T2, and C1R cells to direct the stable expression and secretion, of a variety of costimulatory molecules and cytokines. In a particular embodiment K32 or U32 aAPCs are used to direct the display of one or more antibody-based stimulatory molecules on the AAPC cell surface. Populations of T cells can be expanded by aAPCs expressing a variety of costimulatory molecules including, but not limited to, CD137L (4-1BBL), CD134L (OX40L), and/or CD80 or CD86. Finally, the aAPCs provide an efficient platform to expand genetically modified T cells and to maintain CD28 expression on CD8 T cells. aAPCs provided in WO 03/057171 and US2003/0147869 are hereby incorporated by reference in their entirety.

In a particular embodiment, one or more polynucleotides encoding a MAGEA4 TCR or MAGEA4 eTCR and a chimeric TGFβ receptor are introduced into the population of T cells. In a particular embodiment, a polynucleotide encoding a chimeric TGFβ receptor is introduced into a population of T cells that express a MAGEA4 TCR or MAGEA4 eTCR. In a particular embodiment, a polynucleotide encoding a MAGEA4 TCR or MAGEA4 eTCR is introduced into a population of T cells that express a chimeric TGFβ receptor. In a particular embodiment, a polynucleotide encoding a MAGEA4 TCR or MAGEA4 eTCR and a chimeric TGFβ receptor is introduced into a population of T cells. In a particular embodiment, a polynucleotide encoding a MAGEA4 TCR or MAGEA4 eTCR and a polynucleotide encoding a chimeric TGFβ receptor are simultaneously introduced into a population of T cells. The polynucleotides may be introduced into the T cells by microinjection, transfection, lipofection, heat-shock, electroporation, transduction, gene gun, microinjection, DEAE-dextran-mediated transfer, and the like.

In a preferred embodiment, polynucleotides are introduced into a T cell by viral transduction.

Illustrative examples of viral vector systems suitable for introducing a polynucleotide into an immune effector cell or CD34⁺ cell include, but are not limited to adeno-associated virus (AAV), retrovirus, herpes simplex virus, adenovirus, vaccinia virus vectors for gene transfer.

In one embodiment, polynucleotides are introduced into a T cell by AAV transduction.

In one embodiment, polynucleotides are introduced into a T cell by retroviral transduction.

In one embodiment, polynucleotides are introduced into a T cell by lentiviral transduction.

In one embodiment, polynucleotides are introduced into a T cell by adenovirus transduction.

In one embodiment, polynucleotides are introduced into a T cell by herpes simplex virus transduction.

In one embodiment, polynucleotides are introduced into a T cell by vaccinia virus transduction.

H. Compositions and Formulations

The compositions contemplated herein may comprise one or more MAGEA4 TCR polypeptides, MAGEA4 eTCR polypeptides, CTBR polypeptides, polynucleotides, vectors comprising same, genetically modified immune effector cells, etc., as contemplated herein. Compositions include, but are not limited to pharmaceutical compositions. In preferred embodiments, a composition comprises one or more cells modified to express an a MAGEA4 TCR and a CTBR. In preferred embodiments, a composition comprises one or more cells modified to express a MAGEA4 eTCR and a CTBR12 polypeptide.

A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy. In preferred embodiments, a pharmaceutical composition comprises a pharmaceutically acceptable carrier, diluent or excipient and one or more cells that have been modified to express a MAGEA4 TCR and a CTBR, preferably a MAGEA4 eTCR and a CTBR12 polypeptide.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes but is not limited to isotonic saline; Ringer's solution; ethyl alcohol; phosphate buffer solutions; and any other compatible substances employed in pharmaceutical formulations.

In particular embodiments, compositions comprise an amount of immune effector cells expressing a MAGEA4 TCR and a CTBR, preferably a MAGEA4 eTCR and a CTBR12 polypeptide. As used herein, the term "amount" refers to "an amount effective" or "an effective amount" of a genetically modified therapeutic cell, e.g., T cell, to achieve a beneficial or desired prophylactic or therapeutic result, including clinical results.

A "prophylactically effective amount" refers to an amount of a genetically modified therapeutic cells effective to achieve the desired prophylactic result. Typically, but not necessarily, since a prophylactic dose is used in subjects prior to or at an earlier stage of disease, the prophylactically effective amount is less than the therapeutically effective amount.

A "therapeutically effective amount" of a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient). When a therapeutic amount is indicated, the precise amount of the compositions to be administered can be determined by a physician with consideration of individual differences in age, weight, tumor size, extent of infection or metastasis, and condition of the patient (subject).

It can generally be stated that a pharmaceutical composition comprising the T cells described herein may be administered at a dosage of $10^6$ to $10^{13}$ cells/kg body weight, preferably $10^8$ to $10^{13}$ cells/kg body weight, including all integer values within those ranges. The number of cells will depend upon the ultimate use for which the composition is intended as will the type of cells included therein. For uses provided herein, the cells are generally in a volume of a liter or less, can be 500 ml or less, even 250 ml or 100 ml or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^6$, $10^7$, $10^8$, $10^9$, $10^{10}$, $10^{11}$, $10^{12}$ or $10^{13}$ cells. Compositions may be administered multiple times at dosages within these ranges. The cells may be allogeneic, syngeneic, xenogeneic, or autologous to the patient undergoing therapy.

Compositions are preferably formulated for parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, preferably physiological saline, Ringer's solution, or isotonic sodium chloride. The parenteral preparation can be enclosed in ampoules, disposable syringes or multiple dose vials made of glass or plastic. An injectable pharmaceutical composition is preferably sterile.

In one embodiment, the T cell compositions contemplated herein are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better-defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In one preferred embodiment, compositions comprising immune effector cells contemplated herein are formulated in a solution comprising PlasmaLyte A.

In another preferred embodiment, compositions comprising immune effector cells contemplated herein are formulated in a solution comprising a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In a more preferred embodiment, compositions comprising immune effector cells contemplated herein are formulated in a solution comprising 50:50 PlasmaLyte A to CryoStor CS10.

In a particular embodiment, compositions comprise an effective amount of genome edited immune effector cells modified to express a MAGEA4 TCR and a CTBR, preferably a MAGEA4 eTCR and a CTBR12 polypeptide, alone or in combination with one or more therapeutic agents. Thus, the immune effector cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated in particular embodiments include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising genome edited immune effector cells modified to express a MAGEA4 TCR and a CTBR, preferably a MAGEA4 eTCR and a CTBR12 polypeptide may be administered in conjunction with any number of chemotherapeutic agents.

In particular embodiments, a composition comprising immune effector modified to express a MAGEA4 TCR and a CTBR, preferably a MAGEA4 eTCR and a CTBR12 polypeptide is administered with a therapeutic antibody. Illustrative examples of therapeutic antibodies suitable for combination with the modified T cells contemplated in particular embodiments, include but are not limited to, atezolizumab, avelumab, bavituximab, bevacizumab (avastin), bivatuzumab, blinatumomab, conatumumab, crizotinib, daratumumab, duligotumab, dacetuzumab, dalotuzumab, durvalumab, elotuzumab (HuLuc63), gemtuzumab, ibritumomab, indatuximab, inotuzumab, ipilimumab, lorvotuzumab, lucatumumab, milatuzumab, moxetumomab, nivolumab, ocaratuzumab, ofatumumab, pembrolizumab, rituximab, siltuximab, teprotumumab, and ublituximab.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. 22$^{nd}$ Edition. Edited by Loyd V. Allen Jr. Philadelphia, PA: Pharmaceutical Press; 2012, which is incorporated by reference herein, in its entirety.

I. Therapeutic Methods

The immune effector cells, including MAGEA4 TCR T cells or MAGEA4 eTCR T cells, comprising a CTBR contemplated herein provide improved methods of adoptive immunotherapy for use in the prevention, treatment, and amelioration cancers, or for preventing, treating, or ameliorating at least one symptom associated with a cancer.

The immune effector cells that comprise a MAGEA4 TCR or MAGEA4 eTCR and a CTBR contemplated herein provide improved drug products for use in the prevention, treatment, or amelioration of at least one symptom of a cancer, GVHD, an infectious disease, an autoimmune disease, an inflammatory disease, or an immunodeficiency. As used herein, the term "drug product" refers to modified cells produced using the compositions and methods contemplated herein. In particular embodiments, the drug product comprises genetically modified immune effector cells, T cells modified to express a MAGEA4 TCR or MAGEA4 eTCR further modified to express a CTBR polypeptide. Moreover, the modified T cells contemplated in particular embodiments provide safer and more efficacious adoptive cell therapies because they are resistant to T cell exhaustion and display increased durability and persistence in the tumor microenvironment that can lead to sustained therapy.

In particular embodiments, an effective amount of modified immune effector cells or T cells comprising or expressing a MAGEA4 TCR or MAGEA4 eTCR and a CTBR are administered to a subject to prevent, treat, or ameliorate at least one symptom of a cancer, GVHD, an infectious disease, an autoimmune disease, an inflammatory disease, or an immunodeficiency.

In particular embodiments, a method of preventing, treating, or ameliorating at least one symptom of a cancer comprises administering the subject an effective amount of modified immune effector cells or T cells comprising or expressing a CTBR and a MAGEA4 TCR or MAGEA4 eTCR. The genetically modified cells are a more durable and persistent drug product because the cells are more resistant to immunosuppressive signals from the tumor microenvironment by virtue of converting an immunosuppressive TGFβ signal to an immunostimulatory signal.

In particular embodiments, the modified immune effector cells contemplated herein are used in the treatment of solid tumors or cancers.

In particular embodiments, the modified immune effector cells contemplated herein are used in the treatment of solid tumors or cancers including, but not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, the modified immune effector cells contemplated herein are used in the treatment of solid tumors or cancers including, without limitation, liver cancer, pancreatic cancer, lung cancer, breast cancer, bladder cancer, brain cancer, bone cancer, thyroid cancer, kidney cancer, or skin cancer.

In particular embodiments, the modified immune effector cells contemplated herein are used in the treatment of various cancers including but not limited to pancreatic, bladder, and lung.

In particular embodiments, the modified immune effector cells contemplated herein are used in the treatment of liquid cancers or hematological cancers.

In particular embodiments, the modified immune effector cells contemplated herein are used in the treatment of B-cell malignancies, including but not limited to: leukemias, lymphomas, and multiple myeloma.

In particular embodiments, the modified immune effector cells contemplated herein are used in the treatment of liquid cancers including, but not limited to leukemias, lymphomas, and multiple myelomas: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CIVIL), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sézary syndrome, precursor T-lymphoblastic lymphoma, multiple myeloma, overt multiple myeloma, smoldering multiple myeloma, plasma cell leukemia, nonsecretory myeloma, IgD myeloma, osteosclerotic myeloma, solitary plasmacytoma of bone, and extramedullary plasmacytoma.

Preferred cells for use in the methods contemplated herein include autologous/autogeneic ("self") cells, preferably hematopoietic cells, more preferably T cells, and more preferably immune effector cells.

In particular embodiments, methods comprising administering a therapeutically effective amount of modified immune effector cells contemplated herein or a composition comprising the same, to a patient in need thereof, alone or in combination with one or more therapeutic agents, are provided. In certain embodiments, the cells are used in the treatment of patients at risk for developing a cancer, GVHD, an infectious disease, an autoimmune disease, an inflammatory disease, or an immunodeficiency. Thus, particular embodiments comprise the treatment or prevention or amelioration of at least one symptom of a cancer, an infectious disease, an autoimmune disease, an inflammatory disease, or an immunodeficiency comprising administering to a subject in need thereof, a therapeutically effective amount of the genome edited cells contemplated herein.

In one embodiment, a method of treating a cancer, GVHD, an infectious disease, an autoimmune disease, an inflammatory disease, or an immunodeficiency in a subject in need thereof comprises administering an effective amount, e.g., therapeutically effective amount of a composition comprising modified immune effector cells contemplated herein. The quantity and frequency of administration will be determined by such factors as the condition of the patient, and the type and severity of the patient's disease, although appropriate dosages may be determined by clinical trials.

In one illustrative embodiment, the effective amount of modified immune effector cells provided to a subject is at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, or at least $10 \times 10^6$ cells/kg, or more cells/kg, including all intervening doses of cells.

In another illustrative embodiment, the effective amount of modified immune effector cells provided to a subject is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, or about $10 \times 10^6$ cells/kg, or more cells/kg, including all intervening doses of cells.

In another illustrative embodiment, the effective amount of modified immune effector cells provided to a subject is from about $2 \times 10^6$ cells/kg to about $10 \times 10^6$ cells/kg, about $3 \times 10^6$ cells/kg to about $10 \times 10^6$ cells/kg, about $4 \times 10^6$ cells/kg to about $10 \times 10^6$ cells/kg, about $5 \times 10^6$ cells/kg to about $10 \times 10^6$ cells/kg, $2 \times 10^6$ cells/kg to about $6 \times 10^6$ cells/kg, $2 \times 10^6$ cells/kg to about $7 \times 10^6$ cells/kg, $2 \times 10^6$ cells/kg to about $8 \times 10^6$ cells/kg, $3 \times 10^6$ cells/kg to about $6 \times 10^6$ cells/kg, $3 \times 10^6$ cells/kg to about $7 \times 10^6$ cells/kg, $3 \times 10^6$ cells/kg to about $8 \times 10^6$ cells/kg, $4 \times 10^6$ cells/kg to about $6 \times 10^6$ cells/kg, $4 \times 10^6$ cells/kg to about $7 \times 10^6$ cells/kg, $4 \times 10^6$ cells/kg to about $8 \times 10^6$ cells/kg, $5 \times 10^6$ cells/kg to about $6 \times 10^6$ cells/kg, $5 \times 10^6$ cells/kg to about $7 \times 10^6$ cells/kg, $5 \times 10^6$ cells/kg to about $8 \times 10^6$ cells/kg, or $6 \times 10^6$ cells/kg to about $8 \times 10^6$ cells/kg, including all intervening doses of cells.

One of ordinary skill in the art would recognize that multiple administrations of the compositions contemplated in particular embodiments may be required to effect the desired therapy. For example, a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of T cells.

In one embodiment, a method of treating a subject diagnosed with a cancer, comprises removing immune effector cells from the subject, modifying the immune effector cells by introducing one or more vectors encoding a MAGEA4 TCR or MAGEA4 eTCR and a chimeric TGFβ receptor and producing a population of modified immune effector cells, and administering the population of modified immune effector cells to the same subject. In a preferred embodiment, the immune effector cells comprise T cells.

The methods for administering the cell compositions contemplated in particular embodiments include any method which is effective to result in reintroduction of ex vivo modified immune effector cells or on reintroduction of the modified progenitors of immune effector cells that on introduction into a subject differentiate into mature immune effector cells. One method comprises modifying peripheral blood T cells ex vivo by introducing one or more vectors encoding a MAGEA4 TCR or MAGEA4 eTCR and a chimeric TGFβ receptor and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

MAGEA4 TCR T Cells that Express a TGFβ Signal Converter Transduce an IL-12 Signal and Secrete Increased IFNγ in Response to MAGEA4 and TGFβ1

Peripheral blood mononuclear cells (PBMCs) from a healthy donor were activated with soluble anti-CD3 (50 ng/ml) and anti-CD28 (50 ng/ml) and transduced (MOI=20) with lentiviral vectors (LVV) expressing (i) a MAGEA4 TCR (e.g., SEQ ID NO:4) or (ii) a MAGEA4 TCR and an IL-12 responsive chimeric TGFβ signal converter (CTBR12), e.g., SEQ ID NOs: 4 and 8, encoded on separate vectors. After 10 days of culture in media containing IL2, the cell product was collected for in vitro analysis and cryopreserved.

CTBR12 Signaling

IL-12 signaling involves receptor dimerization and activation of STAT4 via phosphorylation. STAT4 phosphorylation in response to TGFβ was assessed. Smad2/3 phosphorylation was also assessed to verify that CTBR12 blocks native TGFβ signaling. a MAGEA4 TCR T cells and MAGEA4 TCR/CTBR12 T cells were rested overnight in serum-free media, then exposed to TGFβ1 (10 ng/ml) for 20 minutes. Cells were fixed, permeabilized, and stained with anti-phospho-Smad2/3 (pS465/467) and phospho-STAT4 (pY693). CTBR12 blocked the phosphorylation of Smad2/3 and activated STAT4 in T cells expressing MAGEA4 TCRs (FIG. 1, right most panels). These data indicate that CTBR12 can block native TGFβ signaling and transduce an IL-12 signal when co-expressed with a MAGEA4 TCR.

MAGEA4 TCR Signaling

Figure 2:
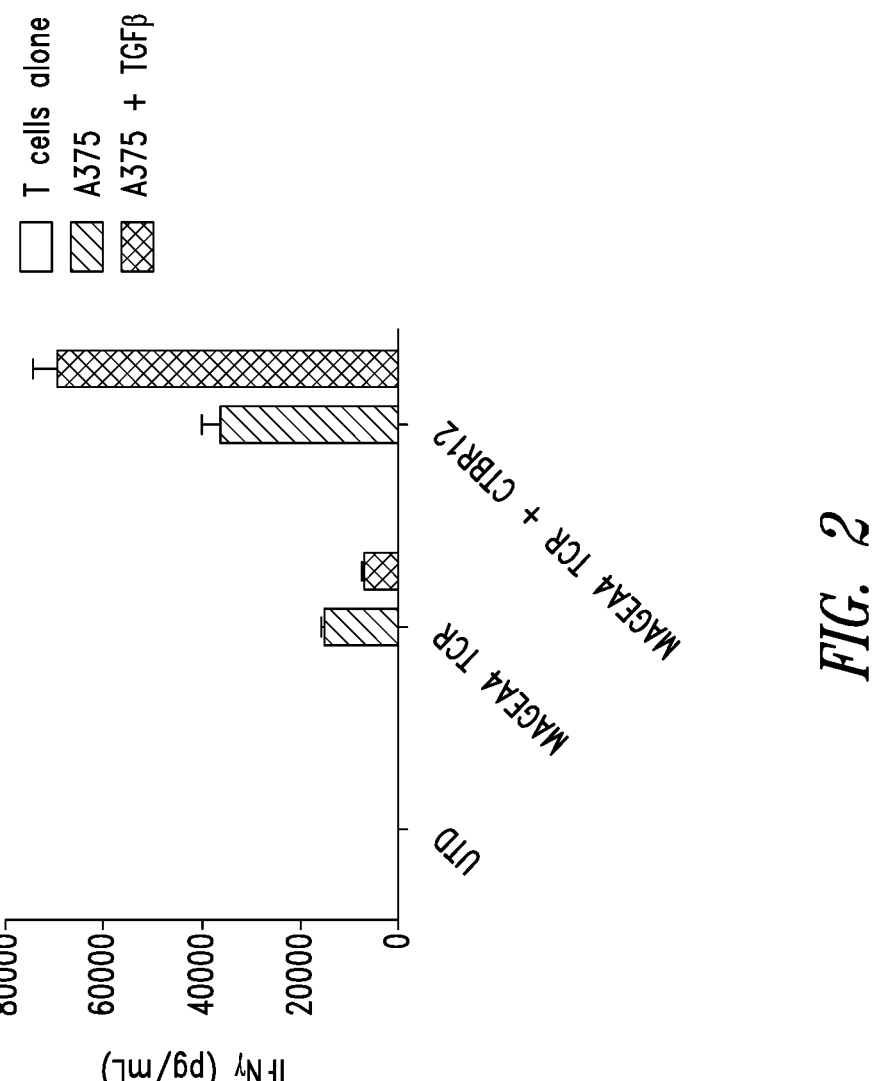
FIG. 2 shows IFNγ secretion from UTD T cells, MAGEA4 TCR T cells, and MAGEA4 TCR/CTBR12 T cells cultured alone or cultured with A375 MAGEA4$^+$ tumor cells at an E:T ratio of 1:1 for 24 hours in the presence or absence of TGFβ1 (10 ng/ml).

Functional TCRs secrete IFNγ in response to antigen, and secretion can be enhanced by IL-12 signaling. Untransduced (UTD) T cells, MAGEA4 TCR T cells, and MAGEA4 TCR/CTBR12 T cells were co-cultured with A375 MAGEA4$^+$ tumor cells at an E:T ratio of 1:1 for 24 hours in the presence or absence of TGFβ1 (10 ng/ml). After 24 hours, the amount of IFNγ secreted into the medium was determined. MAGEA4 TCR/CTBR12 T cells produced significantly greater amounts of IFNγ in the presence of TGFβ1 compared to all other treatment or control conditions. FIG. 2. These data demonstrate that CTBR12 expression in MAGEA4 TCR T cells protects against TGFβ immunosuppression and promotes enhanced effector function in vitro.

Example 2

CTBR12 Expression Enhances MAGEA4 TCR T Cell Efficacy In Vivo

Figure 3:
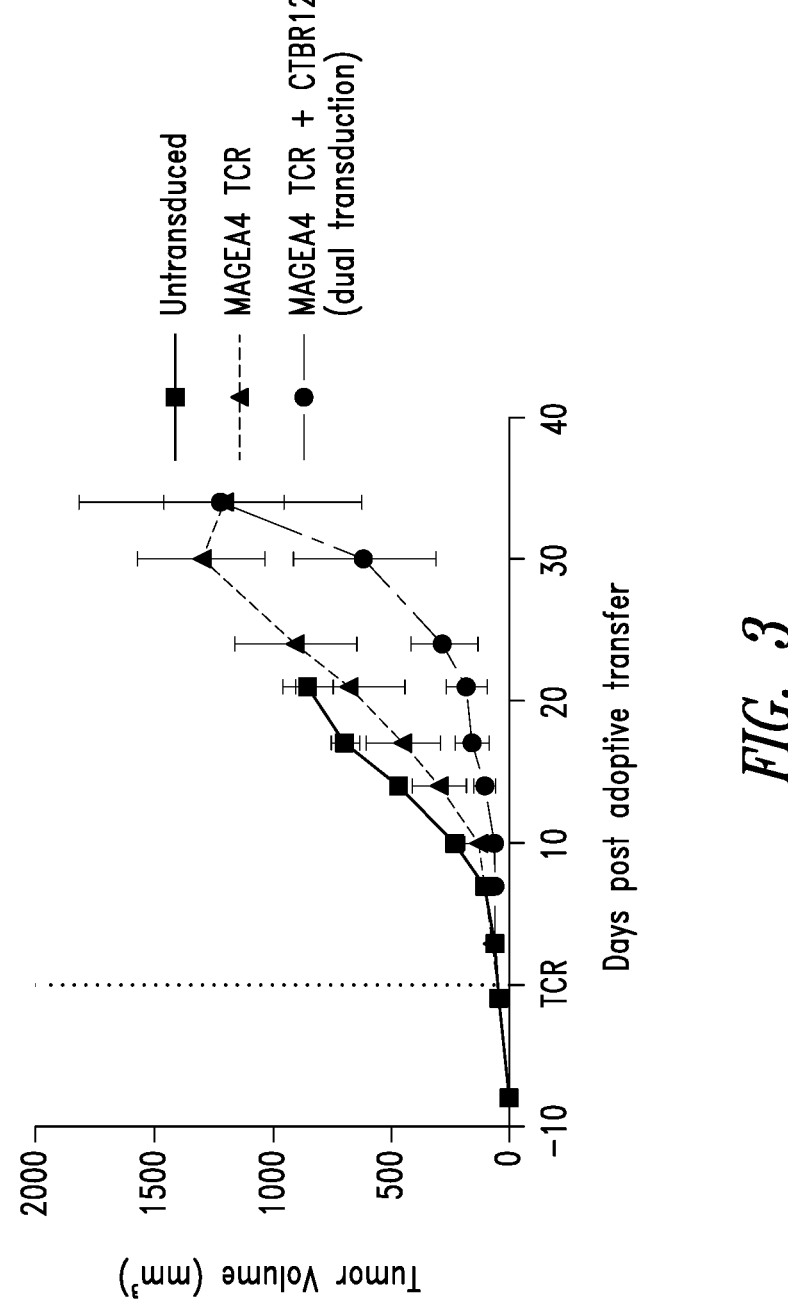
FIG. 3 shows A375 MAGEA4$^+$ tumor cell volume in an NSG tumor xenograft mouse model treated with UTD T cells, MAGEA4 TCR T cells, or MAGEA4 TCR/CTBR12 T cells.

A xenograft NOD.Cg-Prkdcscid IL2rgtm1Wjl/SzJ (NSG) mouse model was used to assess whether CTBR12 expression enhances MAGEA4 TCR T cell efficacy in vivo. NSG mice were implanted with A375 MAGEA4$^+$ tumor cells subcutaneously. Tumor volume was measured twice weekly by caliper and calculated using the formula Tumor Volume=Length×Width×Height×0.52. When the tumors reached a mean volume of 50 mm3, mice were intravenously injected with 0.625×10$^6$ UTD T cells, 0.625×10$^6$ GVY tetramer positive MAGEA4 TCR T cells, or 0.625×10$^6$ GVY tetramer positive MAGEA4 TCR/CTBR12 T cells. MAGEA4 TCR/CTBR12 T cells control tumor volume significantly better than MAGEA4 TCR T cells or UTD control T cells. FIG. 3. These data show that CTBR12 expression enhances the in vivo efficacy of MAGEA4 TCR T cells.

Example 3

Enhanced MAGEA4 TCR T Cells that Express a TGFβ Signal Converter Transduce an IL-12 Signal and Secrete Increased IFNγ in Response to MAGEA4 and TGFβ1

Peripheral blood mononuclear cells (PBMCs) from a healthy donor were activated with soluble anti-CD3 (50 ng/ml) and anti-CD28 (50 ng/ml) and transduced (MOI=20) with lentiviral vectors (LVV) expressing (i) a MAGEA4 pairing enhanced TCR (eTCR), e.g., SEQ ID NO: 7 or (ii) a MAGEA4 eTCR and a CTBR12 receptor (e.g., SEQ ID NOs: 7 and 8) encoded on the same vector. After 10 days of culture in media containing IL2, the cell product was collected for in vitro analysis and cryopreserved.

CTBR12 Signaling

Figure 4:
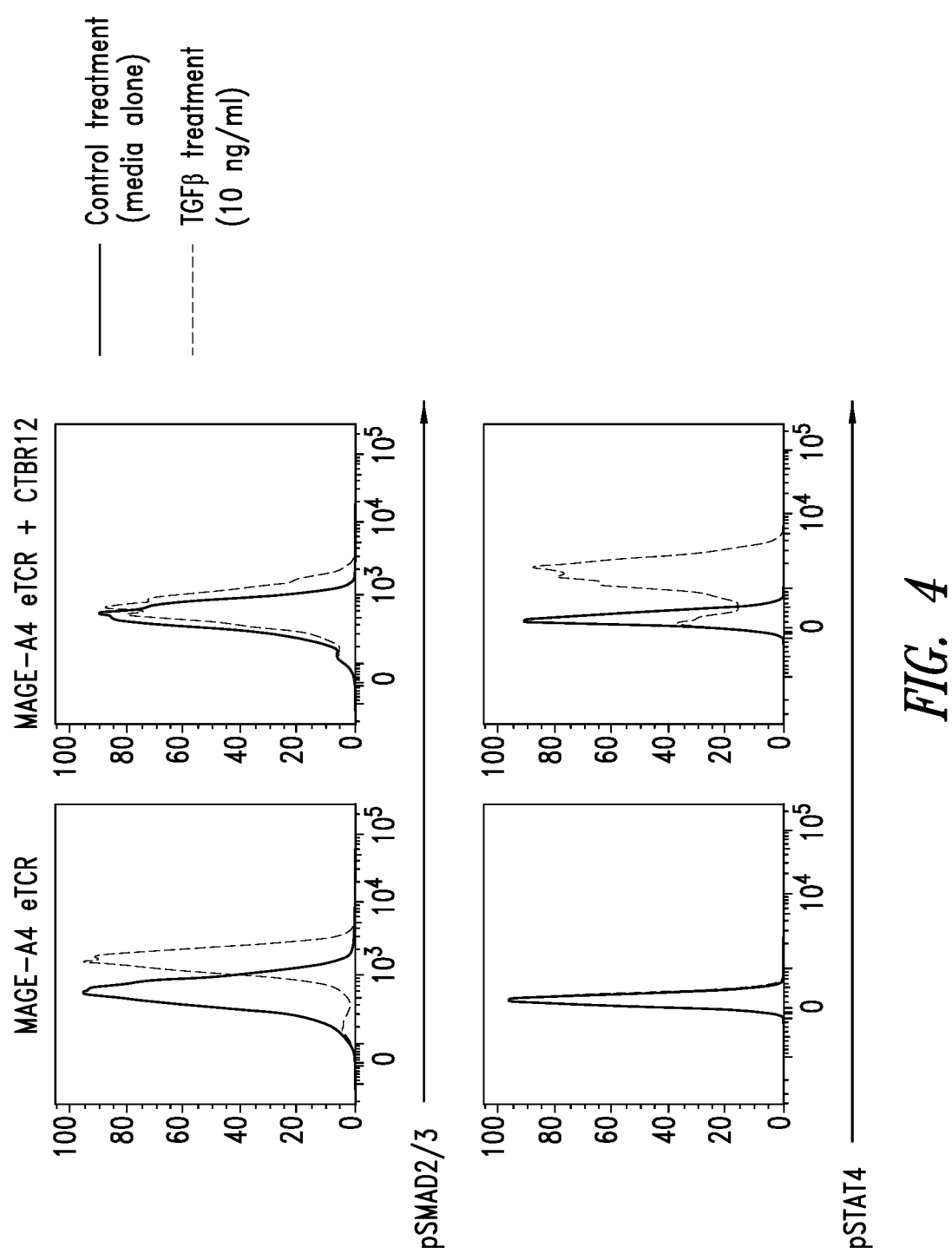
FIG. 4 shows STAT4 and SMAD2/3 phosphorylation in T cells transduced with a LVV encoding a MAGEA4 pairing enhanced TCR (eTCR) and in T cells transduced with a LVV encoding a MAGEA4 eTCR and an IL-12 responsive chimeric TGFβ receptor (CTBR12), cultured in the presence or absence of TGFβ1 for 20 minutes.

IL-12 signaling involves receptor dimerization and activation of STAT4 via phosphorylation. STAT4 phosphorylation in response to TGFβ was assessed. Smad2/3 phosphorylation was also assessed to verify that CTBR12 blocks native TGFβ signaling. a MAGEA4 eTCR T cells and MAGEA4 eTCR/CTBR12 T cells were rested overnight in serum-free media, then exposed to TGFβ1 (10 ng/ml) for 20 minutes. Cells were fixed, permeabilized, and stained with anti-phospho-Smad2/3 (pS465/467) and phospho-STAT4 (pY693). CTBR12 blocked the phosphorylation of Smad2/3 and activated STAT4 in T cells expressing MAGEA4 eTCRs (FIG. 4, right most panels). These data indicate that CTBR12 can block native TGFβ signaling and transduce an IL-12 signal when co-expressed with a MAGEA4 eTCR.

MAGEA4 TCR Signaling

Figure 5:
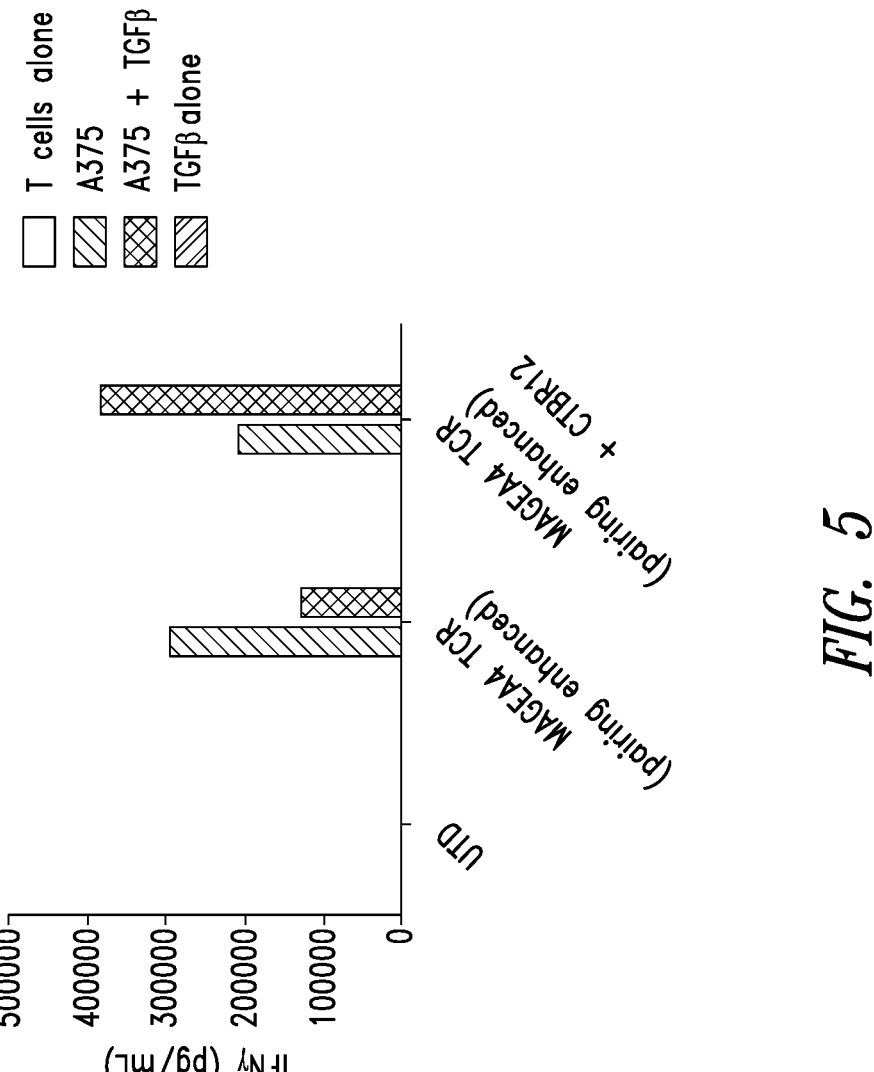
FIG. 5 shows IFNγ secretion from UTD T cells, MAGEA4 eTCR T cells, and MAGEA4 eTCR/CTBR12 T cells cultured alone, cultured with TGFβ1, or cultured with A375 MAGEA4$^+$ tumor cells at an E:T ratio of 1:1 for 24 hours in the presence or absence of TGFβ1 (10 ng/ml).

Functional TCRs secrete IFNγ in response to antigen, and secretion can be enhanced by IL-12 signaling. Untransduced (UTD) T cells, MAGEA4 eTCR T cells, and MAGEA4 eTCR/CTBR12 T cells were co-cultured with A375 MAGEA4$^+$ tumor cells at an E:T ratio of 1:1 for 24 hours in the presence or absence of TGFβ1 (10 ng/ml). After 24 hours, the amount of IFNγ secreted into the medium was determined. TGFβ1 treatment suppressed IFNγ secretion by MAGEA4 eTCR T cells and enhanced IFNγ secretion by MAGEA4 eTCR/CTBR12 T cells. FIG. 5. These data demonstrate that CTBR12 expression in MAGEA4 eTCR T cells protects against TGFβ immunosuppression and promotes enhanced effector function in vitro.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

The invention claimed is:

1. A method of treating a subject having a solid cancer, comprising administering to the subject an effective amount of a T cell comprising a first polynucleotide encoding a MAGEA4 TCR; and a second polynucleotide encoding a fusion polypeptide, wherein the MAGEA4 TCR comprises an alpha chain comprising an amino acid sequence set forth in SEQ ID NO: 2 or 5 and a beta chain comprising an amino acid sequence set forth in SEQ ID NO: 3 or 6, and wherein the fusion polypeptide comprises:

(a) a first polypeptide comprising:
   (i) an extracellular TGFβ1-binding domain of TGFβR2;
   (ii) an IL-12Rβ2 transmembrane domain or an IL-12Rβ1 transmembrane domain; and
   (iii) an IL-12Rβ2 intracellular signaling domain or an IL-12Rβ1 intracellular signaling domain;

(b) a polypeptide cleavage signal; and (c) a second polypeptide comprising:
   (i) an extracellular TGFβ1-binding domain of TGFβR1;
   (ii) an IL-12Rβ2 transmembrane domain or an IL-12Rβ1 transmembrane domain; and
   (iii) an IL-12Rβ2 intracellular signaling domain or an IL-12Rβ1 intracellular signaling domain.

2. The method of claim 1, wherein the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, esophageal cancer, or skin cancer.

3. The method of claim 1, wherein the solid cancer is an esophageal cancer.

4. The method of claim 1, wherein the solid cancer is synovioma.

5. The method of claim 1, wherein the solid cancer is ovarian cancer.

6. The method of claim 1, wherein the solid cancer is non-small cell lung cancer.

7. The method of claim 1, wherein the solid cancer expresses MAGEA4.

8. The method of claim 1, wherein the first polypeptide comprises the IL-12Rβ2 intracellular signaling domain and the second polypeptide comprises the IL-12Rβ1 intracellular signaling domain.

9. The method of claim 8, wherein the first polypeptide comprises the IL-12Rβ2 transmembrane domain and/or the second polypeptide comprises the IL-12Rβ1 transmembrane domain.

10. The method of claim 1, wherein the first polypeptide comprises the IL-12Rβ1 intracellular signaling domain and the second polypeptide comprises the IL-12Rβ2 intracellular signaling domain.

11. The method of claim 10, wherein the first polypeptide comprises the IL-12Rβ1 transmembrane domain and/or the second polypeptide comprises the IL-12Rβ2 transmembrane domain.

12. The method of claim 1, wherein the polypeptide cleavage signal is a viral self-cleaving polypeptide.

13. The cell of claim 12, wherein the polypeptide cleavage signal is a viral self-cleaving 2A polypeptide.

14. The method of claim 1, wherein the MAGEA4 TCR comprises an alpha chain comprising an amino acid sequence set forth in SEQ ID NO: 2 and a beta chain comprising an amino acid sequence set forth in SEQ ID NO: 3.

15. The method of claim 1, wherein the MAGEA4 TCR comprises an alpha chain comprising an amino acid sequence set forth in SEQ ID NO: 5 and a beta chain comprising an amino acid sequence set forth in SEQ ID NO: 6.

16. The method of claim 1, wherein the fusion polypeptide comprises an amino acid sequence set forth in SEQ ID NO: 8.

17. The method of claim 1, wherein the source of the T cell is peripheral blood mononuclear cells, bone marrow, lymph nodes tissue, cord blood, thymus issue, tissue from a site of infection, ascites, pleural effusion, spleen tissue, or tumors.

18. A method of treating a subject having a solid cancer, comprising administering to the subject an effective amount of a T cell comprising a first polynucleotide encoding a MAGEA4 TCR; and a second polynucleotide encoding a fusion polypeptide, wherein the MAGEA4 TCR comprises an alpha chain comprising an amino acid sequence set forth in SEQ ID NO: 2 or 5 and a beta chain comprising an amino acid sequence set forth in SEQ ID NO: 3 or 6, and wherein the fusion polypeptide comprises:

(a) a TGFβR2 polypeptide comprising:
   (i) an extracellular TGFβ1-binding domain of TGFβR2;
   (ii) an IL-12Rβ2 transmembrane domain; and
   (iii) an IL-12Rβ2 intracellular signaling domain;

(b) a viral self-cleaving 2A peptide; and (c) a TGFβR1 polypeptide comprising:
   (i) an extracellular TGFβ1-binding domain of TGFβR1;

(ii) an IL-12Rβ1 transmembrane domain; and (iii) an IL-12Rβ1 intracellular signaling domain.

19. The method of claim 18, wherein the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, esophageal cancer, or skin cancer.

20. The method of claim 18, wherein the solid cancer is an esophageal cancer.

21. The method of claim 18, wherein the solid cancer is synovioma.

22. The method of claim 18, wherein the solid cancer is ovarian cancer.

23. The method of claim 18, wherein the solid cancer is non-small cell lung cancer.

24. The method of claim 18, wherein the solid expresses MAGEA4.

25. The method of claim 18, wherein the MAGEA4 TCR comprises an alpha chain comprising an amino acid sequence set forth in SEQ ID NO: 2 and a beta chain comprising an amino acid sequence set forth in SEQ ID NO: 3.

26. The method of claim 18, wherein the MAGEA4 TCR comprises an alpha chain comprising an amino acid sequence set forth in SEQ ID NO: 5 and a beta chain comprising an amino acid sequence set forth in SEQ ID NO: 6.

27. The method of claim 18, wherein the source of the T cell is peripheral blood mononuclear cells, bone marrow, lymph nodes tissue, cord blood, thymus issue, tissue from a site of infection, ascites, pleural effusion, spleen tissue, or tumors.

28. A method of treating a subject having a solid cancer, comprising administering to the subject an effective amount of a T cell comprising a first polynucleotide encoding a MAGEA4 TCR; and a second polynucleotide encoding a fusion polypeptide, wherein the MAGEA4 TCR comprises an alpha chain comprising an amino acid sequence set forth in SEQ ID NO: 2 or 5 and a beta chain comprising an amino acid sequence set forth in SEQ ID NO: 3 or 6, and wherein the fusion polypeptide comprises:

(a) a TGFβR2 polypeptide comprising:

(i) an extracellular TGFβ1-binding domain of TGFβR2;

(ii) an IL-12Rβ1 transmembrane domain; and (iii) an IL-12Rβ1 intracellular signaling domain;

(b) a viral self-cleaving 2A peptide; and (c) a TGFβR1 polypeptide comprising:

(i) an extracellular TGFβ1-binding domain of TGFβR1;

(ii) an IL-12Rβ2 transmembrane domain; and (iii) an IL-12Rβ2 intracellular signaling domain.

29. The method of claim 28, wherein the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, esophageal cancer, or skin cancer.

30. The method of claim 28, wherein the solid cancer is an esophageal cancer.

31. The method of claim 28, wherein the solid cancer is synovioma.

32. The method of claim 28, wherein the solid cancer is ovarian cancer.

33. The method of claim 28, wherein the solid cancer is non-small cell lung cancer.

34. The method of claim 28, wherein the solid cancer expresses MAGEA4.

35. The method of claim 28, wherein the MAGEA4 TCR comprises an alpha chain comprising an amino acid sequence set forth in SEQ ID NO: 2 and a beta chain comprising an amino acid sequence set forth in SEQ ID NO: 3.

36. The method of claim 28, wherein the MAGEA4 TCR comprises an alpha chain comprising an amino acid sequence set forth in SEQ ID NO: 5 and a beta chain comprising an amino acid sequence set forth in SEQ ID NO: 6.

37. The method of claim 28, wherein the source of the T cell is peripheral blood mononuclear cells, bone marrow, lymph nodes tissue, cord blood, thymus issue, tissue from a site of infection, ascites, pleural effusion, spleen tissue, or tumors.

38. A T cell comprising a first polynucleotide encoding a MAGEA4 TCR; and a second polynucleotide encoding a fusion polypeptide wherein the MAGEA4 TCR comprises an alpha chain comprising an amino acid sequence set forth in SEQ ID NO: 2 or 5 and a beta chain comprising an amino acid sequence set forth in SEQ ID NO: 3 or 6, and wherein the fusion polypeptide comprises SEQ ID NO: 8.

39. The cell of claim 38, wherein the MAGEA4 TCR comprises an alpha chain comprising an amino acid sequence set forth in SEQ ID NO: 2 and a beta chain comprising an amino acid sequence set forth in SEQ ID NO: 3.

40. The cell of claim 38, wherein the MAGEA4 TCR comprises an alpha chain comprising an amino acid sequence set forth in SEQ ID NO: 5 and a beta chain comprising an amino acid sequence set forth in SEQ ID NO: 6.

41. The cell of claim 38, wherein the source of the T cell is peripheral blood mononuclear cells, bone marrow, lymph nodes tissue, cord blood, thymus issue, tissue from a site of infection, ascites, pleural effusion, spleen tissue, or tumors.

42. A method of treating a subject having a solid cancer, comprising administering to the subject an effective amount of the T cell of claim 38.

43. The method of claim 42, wherein the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, esophageal cancer, or skin cancer.

44. The method of claim 42, wherein the solid cancer is an esophageal cancer.

45. The method of claim 42, wherein the solid cancer is synovioma.

46. The method of claim 42, wherein the solid cancer is ovarian cancer.

47. The method of claim 42, wherein the solid cancer is non-small cell lung cancer.

48. The method of claim 42, wherein the solid cancer expresses MAGEA4.

* * * * *